US007759082B2

(12) United States Patent
Bowlin et al.

(10) Patent No.: US 7,759,082 B2
(45) Date of Patent: Jul. 20, 2010

(54) ELECTROPROCESSED FIBRIN-BASED MATRICES AND TISSUES

(75) Inventors: Gary L. Bowlin, Mechanicsville, VA (US); Gary E. Wnek, Midlothian, VA (US); David G. Simpson, Mechanicsville, VA (US); Philippe Lam, San Bruno, CA (US); Marcus E. Carr, Jr., Midlothian, VA (US)

(73) Assignee: Virginia Commonwealth University Intellectual Property Foundation, Richmond, VA (US)

(*) Notice: Subject to any disclaimer, the term of this patent is extended or adjusted under 35 U.S.C. 154(b) by 410 days.

(21) Appl. No.: 10/764,691

(22) Filed: Jan. 26, 2004

(65) Prior Publication Data

US 2004/0229333 A1 Nov. 18, 2004

Related U.S. Application Data

(63) Continuation of application No. 09/946,158, filed on Sep. 4, 2001, now abandoned, and a continuation of application No. 09/714,255, filed on Nov. 17, 2000, now abandoned, which is a continuation-in-part of application No. 09/654,517, filed on Sep. 1, 2000, now abandoned, which is a continuation-in-part of application No. 09/512,081, filed on Feb. 24, 2000, now abandoned, which is a continuation-in-part of application No. 09/386,273, filed on Aug. 31, 1999, now Pat. No. 6,592,623.

(60) Provisional application No. 60/241,008, filed on Oct. 18, 2000, provisional application No. 60/270,118, filed on Feb. 22, 2001, provisional application No. 60/121,628, filed on Feb. 25, 1999.

(51) Int. Cl.
*C12Q 1/56* (2006.01)
(52) U.S. Cl. ...................................... 435/13
(58) Field of Classification Search ........................ None
See application file for complete search history.

(56) References Cited

U.S. PATENT DOCUMENTS

| 1,975,504 | A | 10/1934 | Formhals |
| 3,892,648 | A | 7/1975 | Phillips et al. |
| 4,043,331 | A | 8/1977 | Martin et al. |
| 4,044,404 | A | 8/1977 | Martin et al. |
| 4,294,677 | A | 10/1981 | Sakagami et al. |
| 4,323,528 | A | 4/1982 | Collins |
| 4,455,206 | A | 6/1984 | Funabashi et al. |
| 4,552,707 | A | 11/1985 | How |
| 4,553,974 | A | 11/1985 | Dewanjee |
| 4,565,736 | A | 1/1986 | Stein et al. |
| 4,657,793 | A | 4/1987 | Fisher |
| 4,738,740 | A | 4/1988 | Pinchuk et al. |
| 4,837,285 | A | 6/1989 | Berg et al. |
| 4,837,379 | A * | 6/1989 | Weinberg ................ 424/548 |
| 5,171,505 | A | 12/1992 | Lock |
| 5,252,285 | A | 10/1993 | Lock |
| 5,256,418 | A | 10/1993 | Kemp et al. |
| 5,292,362 | A | 3/1994 | Bass et al. |
| 5,332,475 | A | 7/1994 | Mechanic |
| 5,378,469 | A | 1/1995 | Kemp et al. |
| 5,460,962 | A | 10/1995 | Kemp |
| 5,580,859 | A | 12/1996 | Felgner et al. |
| 5,655,517 | A | 8/1997 | Coffee |
| 5,693,085 | A | 12/1997 | Buirge et al. |
| 5,723,324 | A | 3/1998 | Bowlin et al. |
| 5,813,614 | A | 9/1998 | Coffee |
| 5,902,741 | A | 5/1999 | Purchio et al. |
| 5,906,934 | A | 5/1999 | Grande et al. |
| 5,908,777 | A | 6/1999 | Lee et al. |
| 5,912,177 | A | 6/1999 | Turner et al. |
| 5,915,377 | A | 6/1999 | Coffee |
| 5,922,356 | A | 7/1999 | Koseki et al. |
| 5,935,437 | A | 8/1999 | Whitmore |
| 5,948,654 | A | 9/1999 | Tranquillo et al. |
| 6,057,137 | A | 5/2000 | Tranquillo et al. |
| 6,068,199 | A | 5/2000 | Coffee |
| 6,093,557 | A | 7/2000 | Pui et al. |

(Continued)

FOREIGN PATENT DOCUMENTS

EP 00/05035 A1 10/1979

(Continued)

OTHER PUBLICATIONS

"PlasmaSeal's Autologous Plasma Concentrate: Plasma Concentrate Sealant," http://www.plasmaseal.com/intro.htm., Jun. 14, 2000, pp. 1-5.
Abstract of RU 2034534, Kirichenko, et al. Derwent World Patents Inc., Dialog File No. 351 Accession No. 10521633.
Abstract of RU2031661, Nauchno-proizvodstvennoe predprijatie "Ehkomedservis," Institut Khirurgii im.A.V.Vishnevskogo RAMN, Derwent, XP 00204663.
Agrawal, C.M. et al., "Technique to Control pH in Vicinity of Biodegrading PLA-PGA Implants", J. Biomed. Mater Res., 1997, pp. 105-114, vol. 38.

(Continued)

*Primary Examiner*—Jon P Weber
*Assistant Examiner*—Satyendra K Singh
(74) *Attorney, Agent, or Firm*—Foley Hoag, LLP

(57) ABSTRACT

The invention is directed to formation and use of electroprocessed fibrin as an extracellular matrix and, together with cells, its use in forming engineered tissue. The engineered tissue can include the synthetic manufacture of specific organs or tissues which may be implanted into a recipient. The electroprocessed fibrin may also be combined with other molecules in order to deliver the molecules to the site of application or implantation of the electroprocessed fibrin. The fibrin or fibrin/cell suspension is electrodeposited onto a substrate to form the tissues and organs.

9 Claims, 5 Drawing Sheets

U.S. PATENT DOCUMENTS

| | | | |
|---|---|---|---|
| 6,096,309 | A | 8/2000 | Prior et al. |
| 6,096,347 | A | 8/2000 | Geddes et al. |
| 6,100,026 | A | 8/2000 | Nova et al. |
| 6,103,255 | A | 8/2000 | Levene et al. |
| 6,105,571 | A | 8/2000 | Coffee |
| 6,105,877 | A | 8/2000 | Coffee |
| 6,106,913 | A | 8/2000 | Scardino et al. |
| 6,110,484 | A | 8/2000 | Sierra |
| 6,110,590 | A | 8/2000 | Zarkoob et al. |
| 6,117,296 | A | 9/2000 | Thomson |
| 6,121,042 | A | 9/2000 | Peterson et al. |
| 6,146,892 | A | 11/2000 | Ma et al. |
| 6,179,872 | B1 | 1/2001 | Bell et al. |
| 6,180,605 | B1 | 1/2001 | Chen et al. |
| 6,180,606 | B1 | 1/2001 | Chen et al. |
| 6,190,893 | B1 | 2/2001 | Shastri et al. |
| 6,197,575 | B1 | 3/2001 | Griffith et al. |
| 6,245,345 | B1 | 6/2001 | Swanbom et al. |
| 6,252,129 | B1 | 6/2001 | Coffee |
| 6,254,627 | B1 | 7/2001 | Freidberg |
| 6,265,333 | B1 | 7/2001 | Dzenis et al. |
| 6,306,424 | B1 | 10/2001 | Vyakarnam et al. |
| 6,308,509 | B1 | 10/2001 | Scardino et al. |
| 6,309,661 | B1 | 10/2001 | Setterstrom et al. |
| 6,318,640 | B1 | 11/2001 | Coffee |
| 6,386,195 | B1 | 5/2002 | Coffee et al. |
| 6,399,362 | B1 | 6/2002 | Pui et al. |
| 7,084,082 | B1 | 8/2006 | Shimizu et al. |
| 2001/0003148 | A1 | 6/2001 | Coffee |
| 2002/0084178 | A1 | 7/2002 | Dubson et al. |
| 2002/0089094 | A1 | 7/2002 | Kleinmeyer et al. |
| 2002/0091437 | A1 | 7/2002 | Tseng et al. |
| 2002/0172705 | A1 | 11/2002 | Murphy et al. |
| 2004/0072756 | A1 | 4/2004 | Wilkie et al. |

FOREIGN PATENT DOCUMENTS

| | | |
|---|---|---|
| EP | 0234841 A2 | 9/1987 |
| EP | 0234842 A2 | 9/1987 |
| EP | 0234842 B1 | 9/1987 |
| EP | 0250102 | 12/1987 |
| EP | 0250164 B1 | 12/1987 |
| EP | 0266035 A1 | 5/1988 |
| EP | 1 006 950 | 6/2000 |
| EP | 1212107 | 6/2002 |
| GB | 1377022 | 12/1974 |
| GB | 2142870 | 12/1985 |
| GB | 2360789 A | 10/2001 |
| JP | 55-6061 | 2/1980 |
| JP | 06108307 | 4/1994 |
| JP | 07097714 | 4/1995 |
| JP | 08035193 A | 2/1996 |
| JP | 08-143449 | 6/1996 |
| JP | 09-47503 | 2/1997 |
| JP | 11-142392 | 5/1999 |
| JP | 2000-271207 | 10/2000 |
| RU | 2031661 | 3/1995 |
| RU | 2031661 C1 | 3/1995 |
| RU | 2034534 C1 | 5/1995 |
| WO | WO 91/01695 A1 | 2/1991 |
| WO | WO-94/13266 A1 | 6/1994 |
| WO | WO-95/25481 | 9/1995 |
| WO | WO-95/26235 | 10/1995 |
| WO | WO-96/39101 | 12/1996 |
| WO | WO 97/13849 A1 | 4/1997 |
| WO | WO 98/03267 A | 1/1998 |
| WO | WO 98/56894 A1 | 12/1998 |
| WO | WO 99/66964 | 12/1999 |
| WO | WO 00/67694 A1 | 11/2000 |
| WO | WO 00/72857 A1 | 12/2000 |
| WO | WO-01/15754 | 1/2001 |
| WO | WO 01/26610 A1 | 4/2001 |
| WO | WO-01/26702 | 4/2001 |
| WO | WO 01/27365 A1 | 4/2001 |
| WO | WO 01/51690 A1 | 7/2001 |
| WO | WO-01/54667 | 8/2001 |
| WO | WO 01/74431 A2 | 10/2001 |
| WO | WO-01/80921 | 11/2001 |
| WO | WO-02/00149 | 1/2002 |
| WO | WO-02/13786 | 2/2002 |
| WO | WO-02/18441 | 3/2002 |
| WO | WO-02/32642 | 4/2002 |
| WO | WO-2004/028404 | 4/2004 |
| WO | WO-2004/028547 | 4/2004 |

OTHER PUBLICATIONS

Akins, R.E. et al., "Neonatal Rat Heart Cells Cultured in Simulated Microgravity",In Vitro Cell. Dev. Biol.—Animal, 1997, pp. 337-343, vol. 33.

Amsden et al., "An examination of factors affecting the size, distribution and release characteristics of polymer microbeads made using electrostatics", Journal of Controlled Release, 1997, pp. 183-196, vol. 43.

Baker, T.L. et al., "Three-Dimensional Culture of Bovine Chondrocytes in Rotating-Wall Vessels", In Vitro Cell. Dev. Biol. —Animal, 1997, pp. 358-365, vol. 33.

Baroffio, A. et al., "Identification of self-renewing myoblasts in the progeny of single human muscle satellite cells", Differentiation, 1996, pp. 47-57, vol. 60.

Beck, L., Jr. et al., "Vascular development: cellular and molecular regulation", J. FASEB, 1997, pp. 365-373, vol. 11.

Bohr, D.F. et al., "The Cardiovascular System", Handbook of Physiology, American Physiological Society, 1980, pp. 1-31, vol. II, sec. 2.

Boland et al., "Electrospinning of Tissue Engineering Scaffolds," Paper Presented at American Chemical Society Div. Of Polymeric Materials: Science and Engineering, Presented Aug. 26, 2001, Chicago, IL, Publication approximately Jul. 2001.

Boland et al., "Tailoring a Poly (Glycolic Acid) Tissue Engineering Scaffold by Utilizing Electrostatic Processing," Abstract of Presentation at the 4th International Symposium on Frontiers in Biomedical Polymers, Williamsburg, VA, May 16, 2001.

Bowlin et al., "Electric Field-Mediated Processing of Biomaterials: Toward Nanostructured Biomimetic Systems," Abstract of Presentation at SPIE Annual Meeting, Newport Beach, CA, presented Mar. 8, 2001.

Bowlin et al., "Electrospinning of Biomaterials," Abstract for Presentation at the Second Conference on the Development of Technology in Medicine for Virginia, at the University of Virginia, Presented Nov. 2, 1999.

Bowlin et al., "Electrospinning of Biomaterials," Paper for Presentation at Fiber Society Spring 2001 Meeting, Raleigh, NC, Presented May 23, 2001.

Bowlin, G., "Biomimicking Small Caliber Vascular Construct Engineering," Abstract for Presentation at 2001 Whitaker Foundation Biomedical Engineering Conference, La Jolla, CA, Presented Aug. 9, 2001.

Bowlin, G., "The New 'Spin' on Tissue Engineering Scaffolds," Abstract for Keynote Address at the 4th International Symposium on frontiers in Biomedical Polymers, Williamsburg, VA, Presented May 17, 2001.

Buchko, C.J. et al., "Processing and Microstructural Characterization of Porous Biocompatible Protein Polymer Thin Films", Polymer, 1999, pp. 7397-7407, vol. 40.

Bush, R.L. et al., "Regulation of new blood vessel growth into ischemic skeletal muscle", Journ. of Vascular Surgery, 1998, pp. 919-928, vol. 28.

Cavallaro, J.F. et al., "Collagen Fabrics as Biomaterials", Biotechnology and Bioengineering, 1994, pp. 781-791, vol. 43.

Chen, Da-Ren et al., "Electrospraying of Conducting Liquids for Monodisperse Aerosol Generation in the 4nm to 1.8μm Diameter Range", 1995, pp. 963-977, J. Aerosol Science, 1995, pp. 963-977, vol. 26.

Chen, Da-Ren et al., "Experimental Investigation of Scaling Laws for Electrospraying: Dielectric Constant Effect", Aerosol Science and Technology, 1997, pp. 367-380, vol. 27.

Chen, H.H., et al., "The Use of Collagen Polymer Tube and Fibrin Clot in Peripheral Nerve Repair," Proc. National Science Council (ROC), 1994, pp. 58-63, vol. 18, No. 2.

Ekomedservis: WPI World Patent Information Derwent, Derwent, GB', WPI World Patent Information Derwent, Derwnet, GB, vol. 44, Nr. 95, London, GB, (XP002046663).

Gospodarowicz, D., et al., "The Extracellular Matrix and the Control of Proliferation of Vascular Endothelial and Vascular Smooth Muscle Cells," J. Supramolecular Structure, 1980, pp. 339-372, vol. 13.

Harris, A.K., et al., "Fibroblast traction as a mechanism for collagen morphogenesis", Nature, 1981, pp. 249-251, vol. 290.

Hasegawa, M. et al., "Mechanical Properties of Synthethic Arterial Grafts", J. Biomechanics, 1979, pp. 509-517, vol. 12.

Herbert, C.B., et al., "Effects of fibrin micromorphology on neurite growth from dorsal root ganglia cultured in three-dimensional fibrin gels," J. Biomed Mater Res., 1998, pp. 551-559, vol. 40.

Hirai, J. et al., "Highly Oriented, Tubular Hybrid Vascular Tissue for a Low Pressure Circulatory System", ASAIO Journal, 1994, pp. M383-M388, vol. 40.

Hopkins, S.P. et al., "Controlled delivery of vascular endothelial growth factor promotes neovascularization and maintains limb function in a rabbit model of ischemia", Journ. Vascular Surgery, 1998, pp. 886-895, vol. 27, No. 5.

How, T.V. et al., "Engineering design of vascular prostheses", Proc Instn Mech Engrs, 1992, pp. 61-71, vol. 206.

Huang, D. et al., "Mechanisms and Dynamics of Mechanical Strengthening in Ligament-Equivalent Fibroblast-Populated Collagen Matrices", Annals of Biomedical Engineering, 1993, pp. 289-305, vol. 21.

Huang, L. et al., "Generation of Synthetic Elastin-Mimetic Small Diameter Fibers and Fiber Networks", Macromolecules, 2000, pp. 2989-2997, vol. 33.

Huang, L. et al., "High-Resolution Analysis of Engineered Type I Collagen Nanofibers by Electron Microscopy," Scanning, 2001, pp. 372-375, vol. 23.

Kanda, K., et al., "Mechanical Stress-Induced Orientation and Ultrastructural Change of Smooth Muscle Cells Cultured in Three-Dimensional Collagen Lattices", Cell Transplantation, 1994, pp. 481-492, vol. 3.

Kato, Y.P. et al., "Formation of continuous collagen fibres: evaluation of biocompatibility and mechanical properties", Biomaterials, 1990, pp. 169-175, vol. 11.

Kato, Y.P. et al., "Mechanical properties of collagen fibres: a comparison of reconstituted and rat tail tendon fibres" Biomaterials, 1989, pp. 38-42, vol. 10.

Kim, B-S et al., "Engineering smooth muscle tissue with a predefined structure", J. Biomed. Mater Res., 1998, pp. 322-332, vol. 41.

Kim, B-S et al., "Optimizing Seeding and Culture Methods to Engineer Smooth Muscle Tissue on Biodegradable Polymer Matrices", Biotechnology Bioengineering, 1998, pp. 46-54, vol. 57.

Koh, G.Y. et al., "Long-term survival of AT-1 cardiomyocyte grafts in syngeneic myocardium", Amer. Journ. Physiol., 1993. pp. H1727-H1733, vol. 264.

Li, R-K et al., "In Vivo Survival and Function of Transplanted Rat Cardiomyocytes", Circulation Research, 1996, pp. 283-288, vol. 78, No. 2.

Mandanas, R.A., "Formation of fibrin clots in cryopreserved stem cell bags during thawing procedure: lack of impact on engraftment on autologous stem cell transplantation," Bone Marrow Transplantation, 1999, pp. 303-304, vol. 23.

Matthews et al., "Electroprocessing: Fabrication of Novel Biocompatible Materials," Abstract for Presentation at the 4th International Symposium on Frontiers in Biomedical Polymers, Williamsburg, VA, Presented May 16, 2001.

Matthews et al., "Vascular Engineering Utilizing Electrospun Collagen," Abstract for Presentation at Engineering Tissues, Hilton Head Island, SC, Feb. 24, 2001.

Molnar, G. et al., "Skeletal Muscle Satellite Cells Cultured in Simulated Microgravity", In Vitro Cell. Dev. Biol.—Animal, 1997, pp. 386-391, vol. 33.

Morozov, V.N. et al., "Atomic force microscopy of structures produced by electrospraying polymer solutions", International Journal of Mass Spectrometry, 1998, pp. 143-159, vol. 178.

Morozov, V.N. et al., "Electrospray Deposition as a Method to Fabricate Functionally Active Protein Films", Analytical Chemistry, Apr. 1, 1999, pp. 1415-1420, vol. 71, No. 7.

Murry, C.E. et al., "Skeletal Myoblast Transplantation for Repair of Myocardial Necrosis", Journ. Clin. Invest., 1996, pp. 2512-2523, vol. 98, No. 11.

Niklason, L.E. et al., "Functional Arteries Grown in Vitro", Science, 1999, pp. 489-493, vol. 284.

Okano et al., "Hybrid Muscular Tissues: Preparation of Skeletal Muscle Cell-Incorporated Collagen Gels," Cell Transplantation, 1997, pp. 109-118, vol. 6, No. 2.

Okano, T. et al., "Tissue Engineered Skeletal Muscle: Preparation of Highly Dense, Highly Oriented Hybrid Muscular Tissue", Cell Transplantation, 1998, pp. 71-82, vol. 7, No. 1.

Okano, T. et al., "Tissue Engineering of Skeletal Muscle, Highly Dense, Highly Oriented Hybrid Muscular Tissues Biomimicking Native Tissues", ASAIO Journal, 1997, pp. M749-M753, vol. 43.

Pawlowski et al., "Electrospinning a Biodegradable Vascular Tissue Engineering Scaffold," Abstract for Presentation at the 4th International Symposium on Frontiers in Biomedical Polymers, Williamsburg, VA, Presented May 16, 2001.

Pellegrini, G., et al., "The Control of Epidermal Stem Cells (Holoclones) in the Treatment of Massive Full-Thickness Burns with Autologous Keratinocytes Cultured on Fibrin," Transplantation, Sep. 27, 1999, pp. 868-879, vol. 68, No. 6.

Pins, G.D. et al., "Effects of Static Axial Strain on the Tensile Properties and Failure Mechanisms of Self-Assembled Collagen Fibers", J. Appl. Polym Sci., 1997, pp. 1429-1440, vol. 63.

Pins, G.D. et al., "Self-Assembly of Collagen Fibers Influence of Fibrillar Alignment and Decorin on Mechanical Properties", Biophysical Journal, 1997, pp. 2164-2172, vol. 73.

Reneker, D.H. et al., "Nanometre diameter fibres of polymer, produced by electrospinning", Nanotechnology, 1996, pp. 216-223, vol. 7.

Rodeo, S.A., "New and Emerging Treatments for Cartilage and Meniscus Injuries," MD Vista Journal of Medicine, 2000, pp. 1-4.

Rohr, S. et al., "Patterned Growth of Neonatal Rat Heart Cells in Culture", Circulation Research, 1991, pp. 114-130, vol. 68.

Samuel, J.L. et al., "Mechanically Induced Orientation of Adult Rat Cardiac Myocytes In Vitro", In Vitro Cell. Dev. Biol., 1990, pp. 905-914, vol. 26.

Schreuder-Gibson, H., "Electrospinning Polymer Fibers", www-sscom.army.mil/warrior/97/apr/yarn.htm, U.S. Army Natick Research, Development & Engineering Center, 1997.

Seliktar, D. et al., "Dynamic Mechanical Conditioning of Collagen-Gel Blood Vessel Constructs Induces Remodeling In Vitro", Annals of Biomedical Engineering, 2000, pp. 351-362, vol. 28.

Shansky, J. et al., "A Simplified Method for Tissue Engineering Skeletal Muscle Organoids In Vitro", In Vitro Cell. Dev. Biol. —Animal, 1997, pp. 659-661, vol. 33.

Shinoka, T. et al., "Creation of Viable Pulmonary Artery Autografts Through Tissue Engineering", Journ. Thorac. Cardiovasc. Surg., 1998, pp. 536-546, vol. 115.

Simpson, D.G. et al., "Modulation of Cardiac Myocyte Phenotype In Vitro by the Composition and Orientation of the Extracellular Matrix", Journal of Cellular Physiology, 1994, pp. 89-105, vol. 161.

Soonpaa, M.H. et al., "Formation of Nascent Intercalated Disks Between Grafted Fetal Cardiomyocytes and Host Myocardium", Science, 1994, pp. 98-101, vol. 264.

Stitzel et al., "Electrospraying and Electrospinning of Polymers for Biomedical Applications. Poly (lactic-co-glycolic acid) and Poly (ethylene-co-vinylacetate)." Proc. 32nd Society for the Advancement of Material and Process Engineering (SAMPE) Meeting, Boston, MA, Presented Nov. 7, 2000.

Stitzel, J., Mechanical Design and Development of a Biomimicking, Biodegradable Vascular Graft, Thesis Submitted at Virginia Commonwealth University, Richmond, VA, Aug. 2000, Indexed Feb. 9, 2001.

Stitzel, J.D., et al., "Arterial Smooth Muscle Cell Proliferation on a Novel Biomimicking, Biodegradable Vascular Graft Scaffold," J. Biomaterials Applications, 2001, pp. 1-12, vol. 15.

Telemeco, T. et al., "Electrospinning Applications in Bioengineering: Fabrication of Bio-Engineered Skeletal Muscle," Poster Presentation at Engineering Tissues, Hilton Head Island, SC, Feb. 25, 2001. (Abstracts available Feb. 21, 2001.).

Tiollier, J. et al., "Fibroblast Behavior on Gels of Type I, III, and IV Human Placental Collagens", Experimental Cell Research, 1990, pp. 95-104, vol. 191.

Van Wachem, P.B. et al., "Myoblast seeding in a collagen matrix evaluated in vitro", Journ. of Biomed. Materials Res., 1996, pp. 353-360, vol. 30.

Vandenburgh, H. et al., "Attenuation of Skeletal Muscle Wasting with Recombinant Human Growth Hormone Secreted from a Tissue-Engineered Bioartificial Muscle", Human Gene Therapy, 1998, pp. 2555-2564, vol. 9.

Vandenburgh, H., "Cell Shape and Growth Regulation in Skeletal Muscle: Exogenous Versus Endogenous Factors", Journ. of Cellular Physiology, 1983, pp. 363-371, vol. 116.

Vandenburgh, H.H. et al., "Mechanically Induced Alterations in Cultured Skeletal Muscle Growth", J. Biomechanics, 1991, pp. 91-99, vol. 24.

Vandenburgh, H.H. et al., "Skeletal muscle growth is stimulated by intermittent stretch-relaxation in tissue culture", American Journal of Physiology, 1989, pp. C674-C682, vol. 256.

Vandenburgh, H.H., "Mechanical forces and their second messengers in stimulating cell growth in vitro", American Journal of Physiology, 1992, pp. R350-R355, vol. 262.

Vandenburgh, H.H., "Mechanical stimulation of organogenic cardiomyocyte growth in vitro", Am. J. Physiol., 1996, pp. C1284-C1292, vol. 270.

Ventura, R., et al., "Experimental Suture of the Peripheral Nerves with 'Fibrin Glue'," Ital. J. Orthop Traumatol, 1980, pp. 407-414, vol. 6 No. 3.

Warner, S.B., et al., "A Fundamental Investigation of the Formation and Properties of Electrospun Fibers," National Textile Center Annual Report, Nov. 1999, pp. 1-10.

Watanabe, E. et al., "Cardiomyocyte Transplantation in a Porcine Myocardial Infarction Model", Cell Transplantation, 1998, pp. 239-246, vol. 7, No. 3.

Weiss, S.W. et al., "Revascularization of Skeletal Muscle Transplanted into the Hamster Cheek Pouch: Electron Microscopy", Microvascular Research, 1983, pp. 65-73, vol. 26.

Williams, L., "Exogenous Fibrin Matrix Precursors Stimulate the Temporal Progress of Nerve Regeneration Within a Silicone Chamber," Neurochemical Research, 1987, pp. 851-860, vol. 12, No. 10.

Wnek, G., "Production of Microfibers by Electrospinning," Abstract for Presentation at Phillip Morris Technical Center, Richmond, VA, Presented Feb. 13, 2001.

Wnek, G., "Thinking Small About Old Polymers at the Medicine/Engineering Interface," Abstract for Presentation at Program in Polymer Science and Technology Seminar Series, Presented at Massachusetts Institute of Technology, Cambridge, MA, May 16, 2001.

Wnek, G., "Thinking Small About Old Polymers at the Medicine/Engineering Interface," Abstract for Presentation at Chemical Engineering Seminar, Worcester Polytechnic Institute, Worcester, MA, Presented Oct. 18, 2001.

Wnek, G., "Electroactive Materials and Systems: Applications to Fuel Cells and Biosensors," Abstract for Presentation of Materials Science and Engineering Seminar, Virginia Polytechnic Institute and State University, Blacksburg, VA, Presented Oct. 22, 1999. www.eng.vt.edu/eng/materials/seminars/fall99/wnek.html.

Wnek, G., "Electrospinning of Biomaterials," Abstract of Presentation at University of Massachusetts Lowell Memorial Service and Technical Symposium Honoring Sukant K. Tripathy, Presented in Lowell, MA, Feb. 16, 2001.

Wnek, G., "Electroactive Materials and Systems: Applications to Fuel Cells and Biosensors", Abstract for Presentation at Molecular Geodesics, Inc., Oct. 13 or 14, 1999.

Wnek, G.E., Bowlin, G.L., and Simpson, D.G., "Electrospraying and Electrospinning of Polymers for Tissue Engineering/Biomaterials Applications." Abstract for Presentation at Poly Millennial 2000 an International Symposium by the Division of Polymer Chemistry/American Chemical Society, Hawaii, Presented Dec. 10, 2000.

Wong, W. H. et al., "Synthesis and Properties of Biodegradable Polymers Used as Synthetic Matrices for Tissue Engineering", Synthetic Biodegradable Polymer Scaffolds, 1997, pp. 51-82, Chp. 4.

Ye, Qing, et al., "Fibrin gel as a three dimensional matrix in cardiovascular tissue engineering," European J. Cardio-thoracic Surgery, 2000, pp. 587-591, vol. 17.

Yeager, A. et al., "New Graft Materials and Current Approaches to an Acceptable Small Diameter Vascular Graft", ASAIO Transactions, 1988, pp. 88-94, vol. 34.

Zeng, L., et al., "Fibrin Sealant Matrix Supports Outgrowth of Peripheral Sensory Axons," Scand J. Plast. Reconstr. Hand Surg., 1995, pp. 199-204, vol. 29.

Zünd, G. et al., "Tissue engineering: A new approach in cardiovascular surgery; Seeding of human fibroblasts followed by human endothelial cells on resorbable mesh," European Journal of Cardio-thoracic Surgery, 1998, pp. 160-164, vol. 13.

Abstract of FR1494094, Polymer-bonded leather-like sheet material, F. Andrieu, Sep. 8, 1967, Derwent.

Abstract of JP 08-035193, Preparation of sheet of nonwoven fabric of collagen fibre—by injecting acidic solution of soluble collagen through spinning dyes into aq. conc. solution of salt, cutting obtd. fibre and paper making, Mitsubishi Rayon Co. Ltd., Feb. 6, 1996, Derwent.

Blau, H.M. et al., "Isolation and characterization of human muscle cells", Proc. Natl. Acad. Sci. USA, 1981, vol. 78, pp. 5623-5627.

Bronzing, J. D. The Biomedical Engineering Handbook, 1995, pp. 637-644.

Brossollet, L.J., "Mechanical issues in vascular grafting: a review", Int. Journ. of Artif. Organs, 1992, vol. 15, pp. 579-584.

Esquivel, C., et al., "Why Small Caliber Vascular Grafts Fail: A Review of Clinical and Experimental Experience and the Significance of the Interaction of Blood at the Interface," J. Surgical Research, 1986, vol. 41, pp. 1-15.

Freed, L. et al. "Biodegradable Polymer Scaffolds for Tissue Engineering," Bio/Technology, 1994, vol. 12, pp. 689-693.

Ghosh, S.K. and Mitra, H.P., "Oblique banding pattern in collagen fibrils reconstitued in vitro after trypsin treatment," Biochim Biophys Acta, 1975, vol. 405, pp. 340-346.

Kanda, K., et al. "In Vitro Reconstruction of Hybrid Vascular Tissue Hierarchic and Oriented Cell Layers," ASAIO Journal, 1993, vol. 39, pp. M561-M565.

Kirichenko et al., Abstract of RU 2034534, Derwent World Patents Inc., Dialog File No. 351 Accession No. 1052-1633.

L'Heureux, N. et al., "A completely biological tissue-engineered human blood vessel," FASEB J., 1998, vol. 12, pp. 47-56.

Mikos, A.G., et al., "Wetting of poly (L-lactic acid) and poly (DL-lactic-co-glycolic acid) foams for tissue culture, Biomaterials, 1994, vol. 15, No. 1, pp. 55-58.

Mooney, D.J., et al., "Design and Fabrication of Biodegradable Polymer Devices to Engineer Tubular Tissues," Cell Transplantation, 1994, vol. 3, No. 2, pp. 203-210.

Pepper, M.S., "Manipulating Angiogenesis", Arteriosclerosis, Thrombosis, and Vascular Biol., 1997, vol. 17, pp. 605-619.

Pistner, H. et al., "Poly(L-lactide): a long-term degradation study in vivo, Part III Analytical characterization", Biomaterials, 1993, vol. 14., pp. 293-298.

Rhodin, J.A.G. et al., Chapter I , "Architecture of the vessel wall," in "The Cardiovascular System", Handbook of Physiology, American Physiological Society, 1980, vol. II, Sec. 2, pp. 1-31.

Sabelman, E.E., et al., "Composite Cell/Tissue Replacement for Nerve and Pressure Sore Repair," http://guide.Stanford.edu/Publications/clinB.html, Jun. 15, 2000, pp. 1-2.

Shieh, S.J., et al., "Effect of Crosslinking on Mechanical Properties of Reconsistuted Collagen Fibers", Proc. Ann. Intl. Conf. Engin. Med. Biol. Soc., 1987, vol. 3, pp. 1465-1466.

Silver, F.H. et al., "Type I Collagen in Solution", The Journal of Biological Chemistry, 1980, vol. 255, pp. 9427-9433.

Sparrow, J.T. et al., "Apolipoprotein E: phospholipid binding studies with synthetic peptides from the carboxyl terminus," Biochemistry 31, 1065-1068 (1992).

Thumb, W. et al., "Temperature inducible beta-sheet structure in the transactivation domains of retroviral regulatory proteins of the Rev family", Spectrochimica Acta 55A, 2729-2743 (1999).

Vandenburgh, H. et al., "In vitro Model for Stretch-Induced Hypertrophy of Skeletal Muscle", Science, 1979, vol. 203, pp. 265-268.

Vandenburgh, H., "Dynamic Mechanical Orientation of Skeletal Myofibers in Vitro", Departmental Biology, 1982, vol. 93, pp. 438-443.

Weinberg, C. et al., "A blood vessel model constructed from collagen and cultured vascular cells," Science, 1986, vol. 231, pp. 397-398.

Supplementary European Search Report dated Sep. 16, 2008 from EP08012320.1-2307.

Cohn, Daniel et al., "Introducing a selectively biodegradable filament would arterial prosthesis: A short-term implantation study", Journ. of Biomed. Materials Res., 1992, pp. 1185-1204, vol. 26.

Connold, A.L. et al., "Survival of embryonic cardiac myocytes transplanted into host rat soleus muscle", Journ. of Muscle Res. and Cell Motility, 1995, pp. 481-489, vol. 16.

Deitzel, J.M. et al., "Generation of Polymer Nanofibers Through Electrospinning", Army Research Laboratory, 1999, pp. 1-33, ARL-TR-1989.

Doshi, J. et al., "Electrospinning Process and Applications of Electrospun Fibers", Journ. of Electrostatics, 1995, pp. 151-160, vol. 35.

Drasler, W. J. et al., "A Spun Elastomeric Graft for Dialysis Access", ASAIO Journal, 1993, pp. 114-119, vol. 39.

Ekomedservis: WPI World Patent Information Derwent, Derwent, GB', WPI World Patent Information Derwent, Derwnet, GB, vol. 44, Nr. 95, London, GB, (XP002046663), Mar. 27, 1995 (ABST).

Ferber, D., "Lab-Grown Organs Begin to Take Shape", Science, 1999, pp. 422-424, vol. 284.

Freed, L.E. et al., "Microgravity Tissue Engineering", In Viro Cell. Dev. Biol.—Animal, 1997, pp. 381-385, vol. 33.

Freyssinet, J-M, et al., "Fibrinogen and fibrin in strong magnetic fields. Complementary results and discussion," Biochimie, 1984, pp. 81-85, vol. 66.

Gershon, B. et al., "Utilization of composite laminate theory in the design of synthetic soft tissues for biomedical prostheses", Biomaterials, Casali Inst. of Applied Chemistry, Grad. School of Applied Science and Tech., The Hebrew Univ. of Jerusalem, Oct. 1990, pp. 548-552, vol. 11, No. 8.

Gibson, P.W. et al., "Electrospun Fiber Mats: Transport Properties", U.S. Army Natick Research, Development and Engineering Center, AICHE Journal, 1999, pp. 190, vol. 45.

Gojo, S. et al., "Transplantation of Genetically Marked Cardiac Muscle Cells", Journ. of Thorac. Cardiovasc. Surg., 1997, pp. 10-18, vol. 113.

Gorodetsky, R., "Fibrin Microbeads (FMB) as biodegradable microcarriers for cultured cells and wound healing," Abstract, http://www.Hadassah.org.il/hadasit/patent17.htm, Jun. 14, 2000, pp. 1.

* cited by examiner

ELECTROPROCESSED FIBRIN-BASED MATRICES AND TISSUES

PRIOR RELATED APPLICATIONS

This application is a Continuation Application of U.S. Ser. No. 09/946,158, filed on Sep. 4, 2001 (now abandoned), which claims the benefit of priority to U.S. Provisional Application Ser. Nos. 60/241,008, filed on Oct. 18, 2000 and 60/270,118, filed on Feb. 22, 2001, and which is also a Continuation-in-Part of U.S. application Ser. No. 09/654,517, filed on Sep. 1, 2000 (now abandoned). This application is also a Continuation-in-Part of U.S. Ser. No. 09/714,255, filed Nov. 17, 2000 (now abandoned), which is a Continuation-in-Part of U.S. Ser. No. 09/512,081, filed Feb. 24, 2000 (now abandoned), which claims the benefit of priority to U.S. Provisional Application Ser. No. 60/121,628, filed Feb. 25, 1999, and which is a Continuation-in-Part of U.S. Ser. No. 09/386,273, filed Aug. 31, 1999 (now U.S. Pat. No. 6,592,623). The contents of each application are incorporated herein in their entirety by this reference.

FIELD OF THE INVENTION

The present invention relates to novel methods of making and using electroprocessed fibrin. The invention comprises the use of electroprocessed fibrin as an extracellular matrix for numerous functions. Further, the invention includes combining electroprocessed fibrin and cells together to form engineered tissue. The engineered tissue can include the synthetic manufacture of specific organs or "organ-like" tissue.

BACKGROUND OF THE INVENTION

Fibrin is a natural clotting agent. Therefore, fibrin and fibrin derivatives have commonly been used in hemostatic applications. Its use in analogous applications and in connection with various reinforcing additives have been known and well-documented.

In another field, tissue and organ replacement in patients with failing or damaged organ function is hampered by several significant problems. First, the source of replacement tissue or a replacement organ is typically a living related or cadaveric donor. Both of these sources are limited in number and carry the risk of exposing a recipient to pathologic viruses. Second, since the source of the replacement tissue or organ (with the exception of a living identical twin donor) is genetically distinct from the recipient, the problems of organ rejection and graft versus host disease are significant. Both of these problems can be treated with immunosuppression, but this can cause significant side effects and dramatically increase the risk of infection in a patient.

In yet another field, the emerging techniques with respect to gene transfer can be dangerous when performed in vivo. In other words, in vivo gene transfer can expose a recipient to various viral complications. Further, there are limitations to known gene therapies, for instance, with respect to engineering viral coats large enough to accept large genes such as the gene for Factor VIII (anti-hemophilic factor).

In a different field of study, the science of chemotherapy for cancer patients is, at least at some level, based on estimates of effectiveness of various treatments in combating a patient's cancer cells. There is no efficient way to identify the response of a patient's cancer cells to chemotherapy in vivo or in vitro.

What is needed is a new method of making a fibrin that provides the capability to use it in hemostasis, drug delivery, delivery of other substances, skin repair, wound treatment, tissue engineering, and various other applications.

SUMMARY OF THE INVENTION

The present invention to overcome the foregoing limitations by providing electroprocessed fibrin and an electroprocessed fibrin matrix, methods for making electroprocessed fibrin and fibrin matrix, and methods of using electroprocessed fibrin and fibrin matrix in a wide variety of applications.

The electroprocessed fibrin of the present invention has several uses. In one application, electroprocessed fibrin may be used as an extracellular matrix. Electroprocessed fibrin may be combined with other natural and non-natural fibers, and also with cells. In the fields of tissue and organ replacement, the use of electroprocessed fibrin, including but not limited to, cells and fibrin, can overcome problems of potential infection and rejection. In the field of gene transfer, the manipulation of cells can occur in vitro, where cells that are cultured to be inserted into an extracellular matrix comprised of electroprocessed fibrin could be more easily manipulated and tested. In the field of wound care, a sheet of electroprocessed fibrin can be used to suppress hemorrhage, for example, using non-autologous electroprocessed fibrin to suppress bleeding in a hemophiliac, at an injury site or a chronic ulcer. The electroprocessed fibrin extracellular matrix implanted with cells may be used to test cell responsiveness to drugs or other test substances. In the context of chemotherapy, the electroprocessed fibrin extracellular matrix implanted with a patient's tumor cells could be used to identify in vitro the susceptibility of those cells to alternative chemotherapy treatments. Each of the foregoing alternatives can result in safer and more predictable medical practices.

The present invention provides an extracellular matrix for promoting cell growth comprising the electroprocessed fibrin matrix. The fibrin can be formed of electrospun fibrin fibers or electroaerosol fibrin droplets. Electroprocessed fibrin may also be made through the use of molecules capable of forming fibrin. Fibrinogen and thrombin are two such molecules, and electroprocessing techniques of the present invention may be used to make electroprocessed fibrin from these or other molecules. Fibrinogen may also be processed by electrospinning or electroaerosol techniques and subsequently converted to electroprocessed fibrin by enzymatic methods.

The present invention also provides an electroengineered tissue comprising electroprocessed fibrin and cells. Any cells may be used. The cells may be applied to the electroprocessed fibrin through many techniques, including electroprocessing the cells together with fibrin or separately. The cells may be stem cells, committed stem cells, or differentiated cells. Cellular differentiation inducers may also be employed, including but not limited to peptide growth factors, drugs, or full or partial gene sequences in the sense or antisense direction. The engineered tissue may have a predetermined shape, and the electroprocessed fibrin and cells are used to form the desired shape.

The present invention includes a method of manufacturing a fibrin-containing extracellular matrix using electroprocessing techniques. These techniques include, but are not limited, to electrospinning, electrospray, electroaerosol, electrosputter, or any other technique achieving electrodeposition onto a substrate or target. The method includes streaming an electrically-charged solution comprising fibrin onto a grounded target substrate under conditions effective to deposit the fibrin on said substrate to form an extracellular matrix. The polarity of the solution and ground may be interchanged. The electrically charged solutions may further comprise any molecules with the capability to make fibrin. In a preferred embodiment, electrically charged solutions may comprise fibrinogen and thrombin, used to make electroprocessed fibrin. Alternatively, the electrically charged solution may comprise plasma and thrombin. The fibrin, or fibrin-forming molecules, streamed on to the substrate may comprise either electrospun fibers or electroaerosol droplets. Carrier molecules, such as polyethylene glycol (PEG), may be used to facilitate electroprocessing. For example, if the preferred solvent for a given component of the system is aqueous (for example a drug compound), the fibrinogen or fibrin may be suspended in water in the presence of high molecular weight PEG. PEG spins readily from water and acts as a carrier to electrodeposit the fibrinogen or the fibrin molecules in a specific site with a specific pattern or random pattern. Carriers may also be used to process fibrinogen/fibrin from pure organic solvents.

The present invention also provides a method for manufacturing a fibrin-containing extracellular matrix having a predetermined shape. The method includes pre-selecting a mold adapted to make the predetermined shape and filling the mold with fibrin or fibrin forming molecules using electroprocessing techniques. Alternatively, the method may comprise pre-selecting a mold adapted to make the predetermined shape wherein the mold comprises a grounded target substrate. Then, one or more electrically charged solutions comprising fibrin, or molecules capable of forming fibrin, are streamed onto the grounded target substrate under conditions effective to deposit the fibrin on the substrate to form the extracellular matrix having the predetermined shape. The fibrin streamed onto the substrate may comprise electrospun fibers or electroaerosol droplets.

In the present method of manufacturing an electroprocessed engineered tissue, electrically charged solutions of the fibrin, or molecules capable of forming fibrin, and cells are electrodeposited onto a grounded target substrate under conditions effective to deposit the fibrin and cells onto the substrate. The fibrin and cells streamed onto the substrate may comprise electrospun fibers or electroaerosol droplets. Any cell may be used. The cells include, but are not limited to the following: stem cells and/or committed stem cells, including but not limited to the following: osteoblasts, myoblasts, neuroblasts, fibroblasts, glioblasts; germ cells, hepatocytes, chondrocytes, smooth muscle cells, cardiac muscle cells, connective tissue cells, epithelial cells, endothelial cells, hormone-secreting cells, cells of the immune system, and neurons. Electroprocessing may be used to deliver cells to a specific site within the body. In some applications it may not be necessary to pre-select the type of stem cell that is to be delivered to a specific site using electroprocessing techniques, because many types of stem cells can be induced to differentiate in an organ specific pattern once delivered to a given organ. For example, a stem cell delivered to the liver may be induced to become a liver cell simply by placing the stem cell within the biochemical environment of the liver. Electrospinning is effective at this type of application because the matrix can be tailored to a specific organ site. Also the electrospun matrix can be "programmed" to be stable or to degrade rapidly.

The present invention provides a method for manufacturing an electroprocessed, fibrin-containing extracellular matrix. The method includes an electrically grounded substrate and further provides one or a plurality of reservoirs containing fibrin solutions or solutions of molecules capable of forming fibrin. In one embodiment, the reservoirs are connected substantially at a single orifice that allows the mixture of solutions from the reservoirs upon exit from the reservoirs. The solutions are electrically charged and the mixture of solutions is streamed onto the substrate to form an extracellular matrix. In an alternative embodiment, the plurality of reservoirs comprises first and second reservoirs. The first reservoir has a solution comprising fibrinogen and the second reservoir has a solution comprising thrombin. Fibrinogen may also be electrospun, with or without a carrier molecule, for example, PEG or collagen, and processed into fibrin subsequent to electroprocessing. It is also possible to electrospin these materials onto a target or solvent bath containing thrombin and other biochemical agents that process fibrinogen to fibrin. It this type of application fibrinogen is electroprocessed and converted to fibrin at some time after its deposition on the target.

The present invention includes the product of the process of electroprocessing fibrinogen and thrombin. This processing may comprise electrospinning fibrinogen and thrombin to make fibrin, it may comprise electrospraying fibrinogen and thrombin droplets, it may comprise electrosputtering fibrinogen and thrombin, or it may comprise electroaerosol deposition of fibrinogen and thrombin. Regardless of the method employed, fibrin is electrodeposited onto a substrate or target. Cross-linking agents may also be employed together with the electroprocessed fibrin. For example, the introduction of covalent bonds by Factor XIIIa increases structural rigidity and delays subsequent matrix dissolution.

One method for making a matrix of electroprocessed fibrin includes providing a substrate and two reservoirs of solutions, one solution comprising fibrinogen and the other solution comprising thrombin or other substances, wherein the reservoirs each have an orifice that allows the solution to leave the reservoir. In one embodiment, each orifice communicates with a common channel to allow the two solutions to be combined and ejected through an orifice to the common channel. Then, either the substrate or the solutions are electrically charged and the other is grounded. The fibrinogen and the thrombin are then streamed from the common orifice onto the substrate to form a matrix. The step of streaming fibrinogen and thrombin may form a matrix of electroprocessed fibrin fibers. This step may, alternatively, form a matrix of electroprocessed fibrin droplets.

In another arrangement, separate reservoirs containing solutions comprising fibrinogen and thrombin do not communicate through a common channel but have individual orifices that permit streaming of the solution from each reservoir. The simultaneous co-streaming of the two solutions permits fibrin to form on the target, or in the atmosphere prior to reaching the target.

In yet another arrangement, a reservoir containing a solution of fibrinogen may be used to electrosputter, electrospray or electrospin fibrinogen onto a target containing a thrombin solution or a surface layer containing thrombin in order form fibrin directly on the target. Carrier molecules may optionally be employed to passively carry fibrinogen to the target or surface layer. Alternatively, a solution of thrombin may be used to electrosputter, electrospray or electrospin thrombin onto a target containing fibrinogen to form fibrin. Since the clotting reaction proceeds with reasonable speed in the presence of calcium ion, a calcium-free fibrinogen plus thrombin, or calcium-free plasma plus thrombin can be electroprocessed onto a target containing calcium. Alternatively, a calcium-free stream of any fibrin-forming molecule can be electrodeposited together with a calcium-containing stream of any fibrin-forming molecule.

A further method for making a matrix of fibrin provides a substrate, a target, and at least two separate reservoir solutions, one including fibrinogen and the other including thrombin, wherein the each reservoir has an orifice that either: a) allows the solution to leave the reservoir and contact the other solution through a common channel in communication with each orifice prior to electroejection of the mixed solutions from an orifice located at an end of the common channel, or b) permits electroejection directly from an opening in communication with the orifice from each reservoir. Then, either the target or the solution is electrically charged and the other is grounded. The substrate is disposed between the orifice and the target. The fibrinogen/thrombin mixture or the separate solutions of fibrinogen and thrombin are then streamed from the reservoir and through the orifice onto the substrate to form a matrix. The step of streaming these fibrinogen and thrombin solutions forms a matrix of fibrin fibers or alternatively, a matrix of fibrin droplets. Further, the substrate may define a preselected shape. The fibrin matrix can be formed in the presence of cross-linking agents or may be treated with cross-linking agents after streaming.

The electroprocessed fibrin of the present invention may be employed as a vehicle or carrier for scaffolds of other extra-cellular matrix proteins, drugs and other substances. If electroprocessed fibrin were combined with other polymers or natural or non-natural fibers, and the polymers were cross-linked in the electroprocessed fibrin, the fibrin would later dissolve through natural or artificial means, leaving the cross-linked scaffold in place.

The electroprocessed fibrin of the present invention may be employed as a vehicle for drug delivery or delivery of other substances, for example, anti-oxidants, vitamins, cosmetics, nucleic acids, vectors, wound care products, and hormones. This electroprocessed fibrin can be used as a "bio-degradable" depot system, placing high concentrations of a substance such as a drug at a specific location. Drug release can be tailored by altering the structure of the electroprocessed fibrin or the rate at which it dissolves. Any drug or other substance may be combined with the electroprocessed fibrin.

The electroprocessed fibrin is particularly useful in application to the dermis and epidermis, for example in therapeutic or in cosmetic applications. For example, the electroprocessed fibrin is useful in vascular grafts for promoting endothelialization. Healing and wound repair, for example with cuts, abrasions or ulcers represents a preferred application of the invention. Such applications may employ antibiotics, antibacterials, anti-inflammatories or substances that promote healing, as known to one of ordinary skill in the art. Other classes of drugs or substances include, but are not limited to, antibiotics, chemotherapy agents, antifungals, analgesics, hormones, emollients, humectants, anti-oxidants, vitamins, rejection drugs, and conditioners. Some preferred drugs or substances include, but are not limited to, estrogen, androgen, cortisone, cyclosporin, peptide growth factors including VEGF (vascular endothial growth factor), NGFs (nerve growth factors), PDGF-AA, PDGF-BB, PDGF-AB, FGFb, FGFa, and BGF (bone growth factors). Topical antibiotics include, but are not limited to, penicillin, gentimycin, tetracycline. Antimycotics may also be employed.

The electroprocessed fibrin, electroprocessed fibrin matrix and/or electroprocessed fibrin and cells of the present invention may be applied to a desired site through any means, including but not limited to oral administration, anal administration, topical application, aerosol application, inhalation, intraperitoneal administration, administration into a body cavity, administration into the lumen or parenchyma of an organ, or spraying directly on a desired site. Spraying may include electrospraying on a desired site. Sites of application may be external, such as on the epidermis, or internal, for example a gastric ulcer, a surgical field or elsewhere. The electroprocessed fibrin of the present invention may be applied in the form of creams, gels, solutions, suspensions, liposomes, particles, or other means known to one of skill in the art of formulation and delivery of therapeutic and cosmetic substances. Ultrafine particle sizes of electroprocessed fibrin may be used for inhalation delivery of therapeutics.

The present invention includes a method for testing the effectiveness molecules on cells contained in an electroprocessed fibrin matrix in vitro. Any cell may be placed in the fibrin matrix and any desired substance may be administered to the cell in the fibrin matrix. Any desired biological response may be evaluated. This method may alternatively include manufacturing electroengineered tissue by streaming an electrically charged solution comprising fibrin and cancer cells on to a grounded target substrate under conditions effective to deposit the fibrin and cancer cells onto the substrate. The present invention includes a method for testing the effectiveness of cancer therapy treatments in vitro. The method includes manufacturing electroengineered tissue comprising fibrin and cancer cells. A plurality of samples of the electroengineered tissue are subjected to a plurality of cancer therapy treatments. The method further includes evaluating the relative effectiveness of the cancer therapy treatments. Also, the cancer cells may be obtained from a patient who is in need of cancer therapy treatments.

Accordingly, it is an object of the present invention to overcome the foregoing limitations and drawbacks by making and using electroprocessed fibrin.

Yet another object of the present invention is to provide an electroprocessed fibrin matrix. By electroprocessing, a fibrin matrix can be formed for use in numerous fields including biomedical applications, among others. Electroprocessed fibrin forms a three-dimensional, space filling network, and can be aligned during formation by flow dynamics. Once formed, the fibrin matrix can be aligned by mechanical traction, magnetic force or other means.

Another object of the present invention is to provide methods for making electroprocessed fibrin and an electroprocessed fibrin matrix.

It is an object of the present invention to use fibrin or any solution capable of forming fibrin in the process of electroprocessing.

It is another object of the present invention to use fibrinogen in combination with thrombin, and/or other agents capable of processing fibrinogen to fibrin, in the process of electroprocessing. Through the electroprocessing method of the present invention, a fibrin matrix can be formed for use in multiple fields including biomedical applications, among others.

It is another object of the present invention to use the present methods to engineer tissues containing electroprocessed fibrin or an electroprocessed fibrin matrix. These tissues may include cells, drugs or other substances.

Still another object of the present invention is to provide a new method of delivery of substances, such as drugs, using electroprocessed fibrin, electroprocessed fibrin matrix and engineered tissue containing electroprocessed fibrin matrix.

Yet another object of the present invention is to provide engineered tissue containing electroprocessed fibrin matrix which can be used as a wound dressing, a nerve guide or as another implantable tissue.

An advantage of the present invention is that autologous fibrin may be employed, thereby minimizing chances for immune rejection of the electroprocessed fibrin matrix or the engineered tissue containing electroprocessed fibrin matrix.

These and other objects, features and advantages of the present invention will become apparent after a review of the following detailed description of the disclosed embodiments and the appended drawings.

DETAILED DESCRIPTION OF THE PREFERRED EMBODIMENTS

Figure 1:
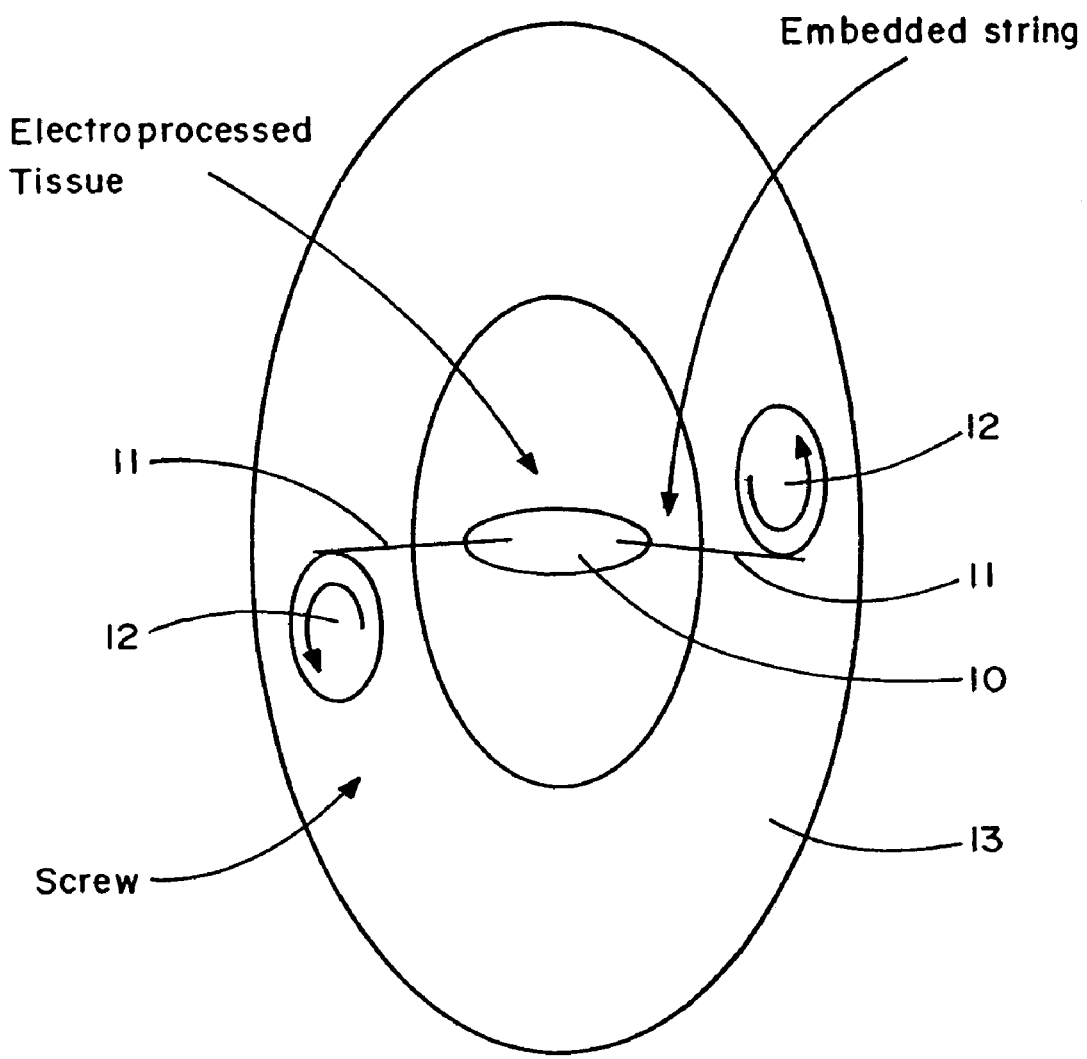
FIG. 1 is a schematic of an apparatus for applying strain to electroprocessed fibrin.
Figure 2:
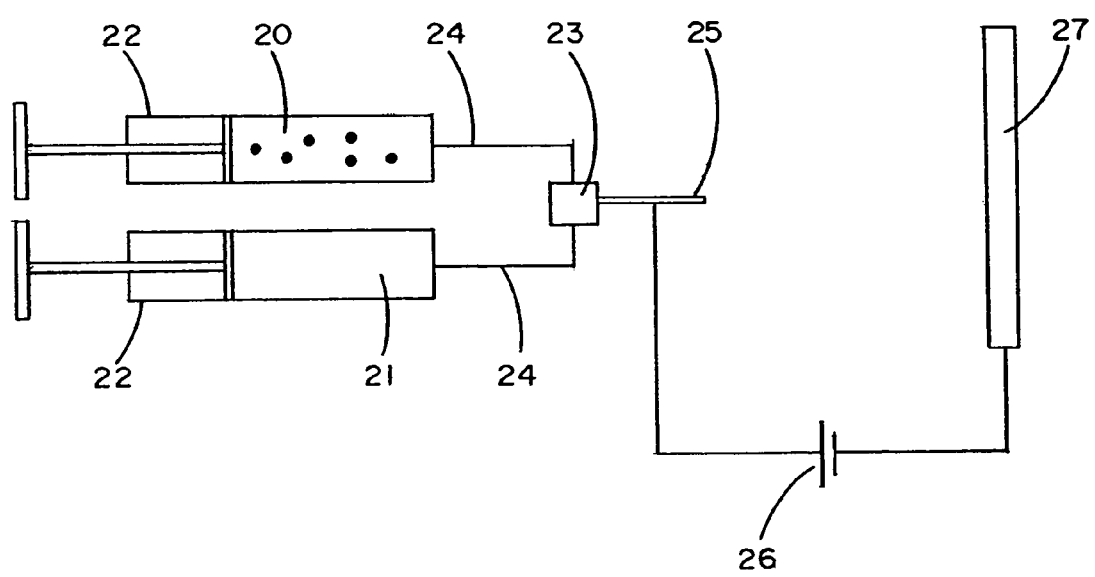
FIG. 2 is a schematic of an electrospinning apparatus.

The terms "electroprocessing" and "electrodeposition" shall be used broadly to cover the methods of electrospinning, electrospraying (electroaerosoling), electrosputtering of fibrin droplets, combinations of electrospinning and electroaerosoling, other combinations thereof, and any other method wherein fibrin, molecules capable of forming fibrin, fibrinogen, thrombin or combinations thereof, are streamed, sprayed, sputtered or dripped across an electric field and toward a target. Similarly, the solution may be streamed from one or more grounded reservoirs in the direction of a charged substrate or from charged reservoirs toward a grounded target. "Electrospinning" means a process in which fibrin fibers are formed from a solution or melt by streaming an electrically charged solution or melt through an orifice. "Electroaerosoling" means a process in which droplets are formed from a solution or melt by streaming an electrically charged polymer solution or melt through an orifice. The term "electroprocessing", therefore, is not limited to the specific examples set forth herein.

For the purposes of the present invention, the term fibrin extracellular matrix refers to any three-dimensional structure onto which or in which cells can attach, multiply and grow. Other common terminology for fibrin extracellular matrices include scaffold, platform and a fascial sheath that could surround a muscle or nerve.

Throughout this application, the term "solution" is used to describe the liquid in the reservoir of the electroprocessing method. In a preferred embodiment, fibrin in a solution is electrodeposited on a target. In the present invention, preferred solutions for formation of fibrin comprise a solution of thrombin and a solution of fibrinogen. Fibrinogen is converted to fibrin monomer by thrombin, which aggregates into fibrin due to electrostatic interactions. This fibrin is not covalently cross-linked. It is to be understood that any solutions capable of forming fibrin following electrospinning, electrospraying or any form of electrodepositing are included within the scope of the present invention. For example, fibrin, fibrin analogs, precursors or active fragments thereof, fibrinogen analogs, precursors or active fragments thereof, and thrombin analogs, precursors or active fragments thereof and other molecules that are capable of forming fibrin may be employed in the present invention. Plasma is a good source of fibrinogen for fibrin formation, and plasma may be electroprocessed for this application. In one embodiment, a patient's blood may be used to prepare fibrin matrix for autologous application. Several enzymes will clot fibrinogen, and any enzyme with this capability is considered within the scope of the present invention. These include but are not limited to, reptilase, batroxobin, and a variety of other snake venom enzymes. In addition, fibrinogen will form a "fibrin-like" matrix by adding large amounts of protamine sulfate. This process has been termed paracoagulation.

In this application, the term "solution" also refers to suspensions containing the fibrin, molecules capable of forming fibrin, cells, substances such as drugs, other molecules or anything to be electrodeposited. "Solutions" may be in organic or biologically compatible forms. This broad definition is appropriate in view of the large number of solvents or other liquids and carrier molecules, such as PEG, that may be used in the many variations of electroprocessing. Non cross-linked fibrin monomer may be electrodeposited or electrospun from solvents such as urea, monochloroacetic acid, or hexafluoroisopropanol (HFIP).

The term "fibrin" is used throughout the present application in its broadest definition. It includes, but is not limited to, fragments, analogs, conservative amino acid substitutions, and substitutions with non-naturally occurring amino acids. There are multiple types of fibrin that are naturally-occurring as well as types that are being synthetically manufactured or produced by genetic engineering. Other types may be found or synthesized in the future, or specific subsets of various fibrin molecules may be isolated with unique effects and may be used to make products like those described herein. All of these types and subsets are encompassed in the use of the term "fibrin" herein. Also, as evidenced by some of the examples, the fibrinogen and/or the thrombin may be mixed with other polymers or other molecules during electroprocessing to obtain specifically desirable properties for given end use of the fibrin or fibrin matrix.

Electroprocessing Methods of Forming Fibrin

Fibrin, or any molecule capable of forming fibrin, can be used in the present invention to form electroprocessed fibrin. Fibrinogen and thrombin are two preferred molecules for making fibrin. Fibrinogen can be electroprocessed in conjunction with or separately from thrombin to form electroprocessed fibrin or an electroprocessed fibrin matrix. This is conducted under conditions that do not allow thrombin to promote the processing of fibrinogen to fibrin. This may be accomplished several ways. For example, the fibrinogen and thrombin can be electroprocessed from a solvent that does not allow thrombin to function. Alternatively, the fibrinogen or thrombin can be packaged in a carrier material. In this application the fibrinogen can be electroprocessed onto the target from one solution source (by itself or with a carrier). The thrombin can be deposited in an electroaerosol manner from a separate source. The thrombin can be encapsulated and sprayed as a fine mist of particles. Alternatively, thrombin and fibrinogen can be mixed with a carrier, such as PEG or collagen.

Fibrin as a preformed gel can be electroprocessed. A fibrin gel may be subjected to pressure, for example using a syringe with a pressure head behind it to extrude the fibrin gel into the electrical field.

The carrier acts to hold the reactants in place until they are initiated. The entire product is preferably stored under dry conditions. When the material is placed in a moist environment, for example a cut, ulcer, or weeping wound, the thrombin is released, processes fibrinogen to fibrin and clot formation occurs. As stated above, it is to be understood that carriers may be used in conjunction with the molecules capable of forming fibrin. For example, fibrinogen can be mixed with PEG, collagen or other known carriers that form filaments. This produces hairy filaments with the hair being fibrin. The fibrin in this type of use cross links the surrounding matrix carrier into a gel. This approach may be used for gelling molecules that do not normally gel. For example, if type IV collagen, or some other collagen, would not form filaments, the fibrinogen, collagen and PEG could be electrosprayed to form an electroprocessed fibrin-containing matrix. Once fibrin formation begins, a fibrin/collagen gel would be produced.

Alternatively, the fibrinogen/fibrin can be sputtered with another molecule that forms a sheet (for example, PGA PLA PGA:PLA, collagen, fibronectin). This sheet could be placed over a wound. If the wound opens the fibrinogen is converted to fibrin and a clot forms. If thrombin is present in the sheet, a clot may be obtained with the addition of water and the release of the thrombin. Such sheets have applications in surgery and wound care, among other uses. It is to be understood that other fibrin forming molecules besides fibrinogen and thrombin may be employed.

In addition to the multiple equipment variations and modifications that can be made to obtain desired results, similarly the solution can be varied to obtain different results. For instance, the solvent or liquid in which the fibrinogen or thrombin is dissolved or suspended may be varied.

The fibrinogen or thrombin can be mixed with other molecules, monomers or polymers to obtained desired results. For instance, polymers can be added to modify the viscosity of the solution. In still a further variation, when multiple reservoirs are used, the ingredients in those reservoirs may be electrosprayed separately or joined at the nozzle so that the ingredients in the various reservoirs may react with each other simultaneously with the streaming of the solution into the electric field. Also, when multiple reservoirs are used, the different ingredients in different reservoirs may be phased in temporally during the processing period. The fibrinogen may be directly altered, for example, by altering the carbohydrate profile of the molecule. Also, other materials may be attached to the fibrin before, during or after electroprocessing of the fibrinogen and or thrombin. Further, the temperature and other physical properties of the process can be modified to obtain different results.

Finally, there are many types of post-process treatments that may be used to modify and adjust the fibrin matrix resulting from the electroprocessing procedure. For instance, the fibrin matrix may be treated with a cross-linking agent, including chemical and UV-light based cross-linking agents. Also, the fibrin matrix may be treated with variations in temperature. Still further chemical variations may be envisioned by those desiring specific end properties of a matrix. Fibrin is formed in different ways, for example by mixing together fibrinogen and thrombin in appropriate concentrations. Building an extracellular matrix comprised of fibrin, therefore, involves different ways of bringing the molecules capable of forming fibrin, such as fibrinogen and thrombin, together through electroprocessing methods. This fibrin may also be manipulated after it is formed with the electroprocessing methods.

In the most fundamental sense, the electroprocessing apparatus for electroprocessing fibrin includes a streaming mechanism and a target substrate. The streaming mechanism includes a reservoir or reservoirs to hold the one or more solutions that are to be streamed in the process. The reservoir or reservoirs have at least one orifice or nozzle to allow the streaming of the solution from the reservoirs. There may be a single nozzle or multiple nozzles in a given electroprocessing apparatus. If there are multiple nozzles, they may be attached to one or more reservoirs containing the same or different solutions. Similarly, there may be a single nozzle that is connected to multiple reservoirs containing the same or different solutions. Also, the size of the nozzle may be varied to provide for increased or decreased flow of the solution out of the reservoir through the nozzle. A pump used in connection with the reservoir may be used to control the flow of solution streaming from the reservoir through the nozzle or nozzles. The pump may be programmed to increase or decrease the flow at different points during electroprocessing.

The target substrate may also be used as a variable feature in the electroprocessing of molecules used to make electroprocessed fibrin. Specifically, the target may be the actual substrate for the molecules used to make electroprocessed fibrin, or electroprocessed fibrin itself is deposited. Alternatively, a substrate may be disposed between the target and the nozzle. For instance, a petri dish can be disposed between a nozzle and a target, and a matrix can be formed in the dish to study cell growth in three dimensions by forming a scaffold in the bottom of the dish. Other variations include non-stick surfaces between the nozzle and target. The target may also be specifically charged (grounded) along a preselected pattern so that the solution streamed from the orifice is directed into specific directions. The electric field may be controlled by a program to create an electroprocessed fibrin matrix having a desired geometry. The target and the nozzle or nozzles may be engineered to be movable with respect to each other thereby allowing additional control over the geometry of the fibrin matrix to be formed. The entire process may be controlled by a microprocessor that is programmed with the specific parameters to obtain a specific, preselected and electroprocessed matrix of fibrin and, if desired, other molecules, monomers or polymers.

Also, as noted in the specific examples that follow, the nozzle or orifice that allows streaming of solution from the reservoir is shown to be charged and the target is shown to be grounded. Those of skill in the electroprocessing arts will recognize that the nozzle and solution may be grounded and the target may be electrically charged. In any event, it is the creation of the electrical field and the effect of the electrical field on the streamed fibrin, or the streamed thrombin and fibrinogen that help create the fibrin.

Figure 3:
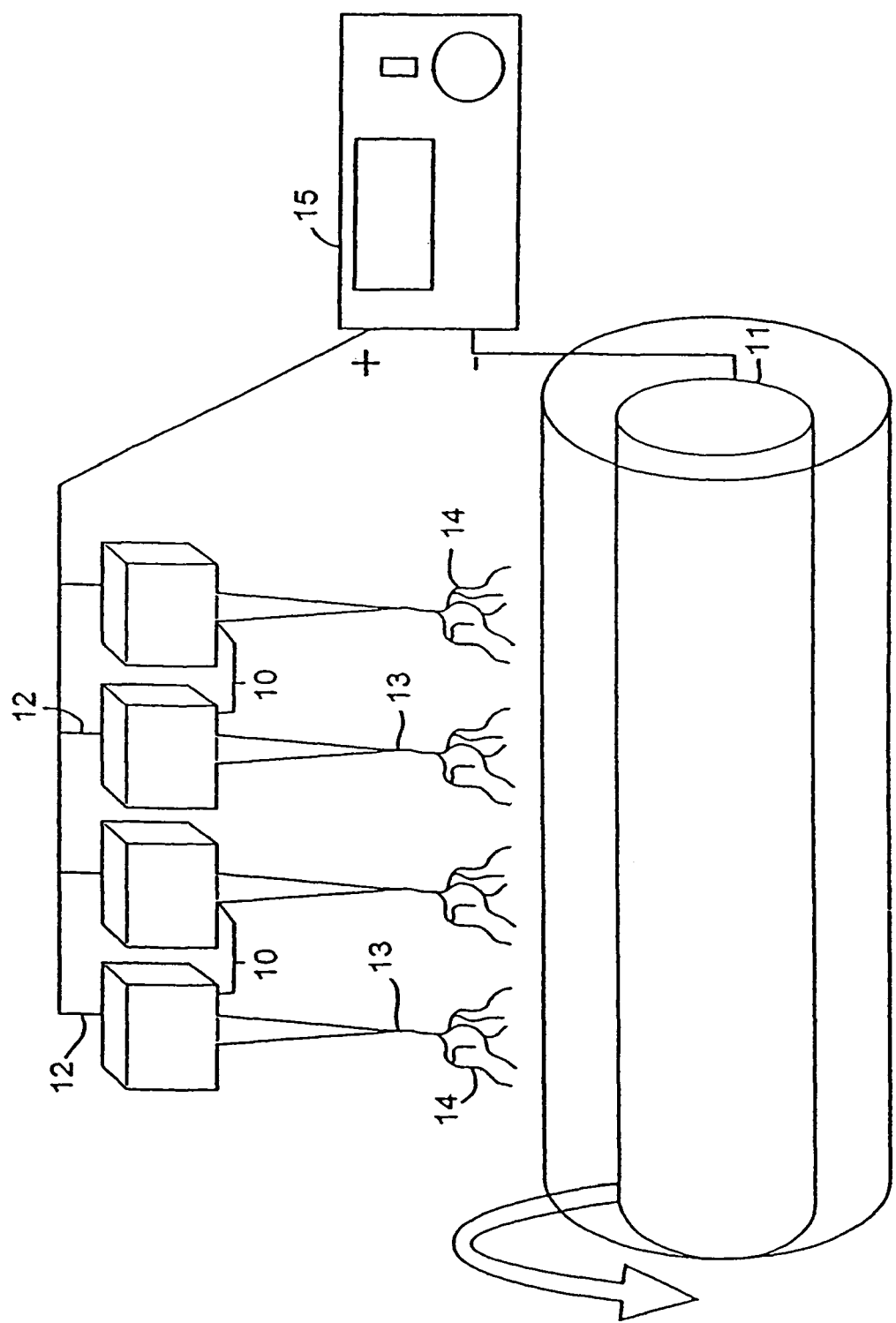
FIGS. 3 and 4 are schematic drawings of an electroprocessing device including the electroprocessing equipment and a rotating wall bioreactor.
Figure 4:
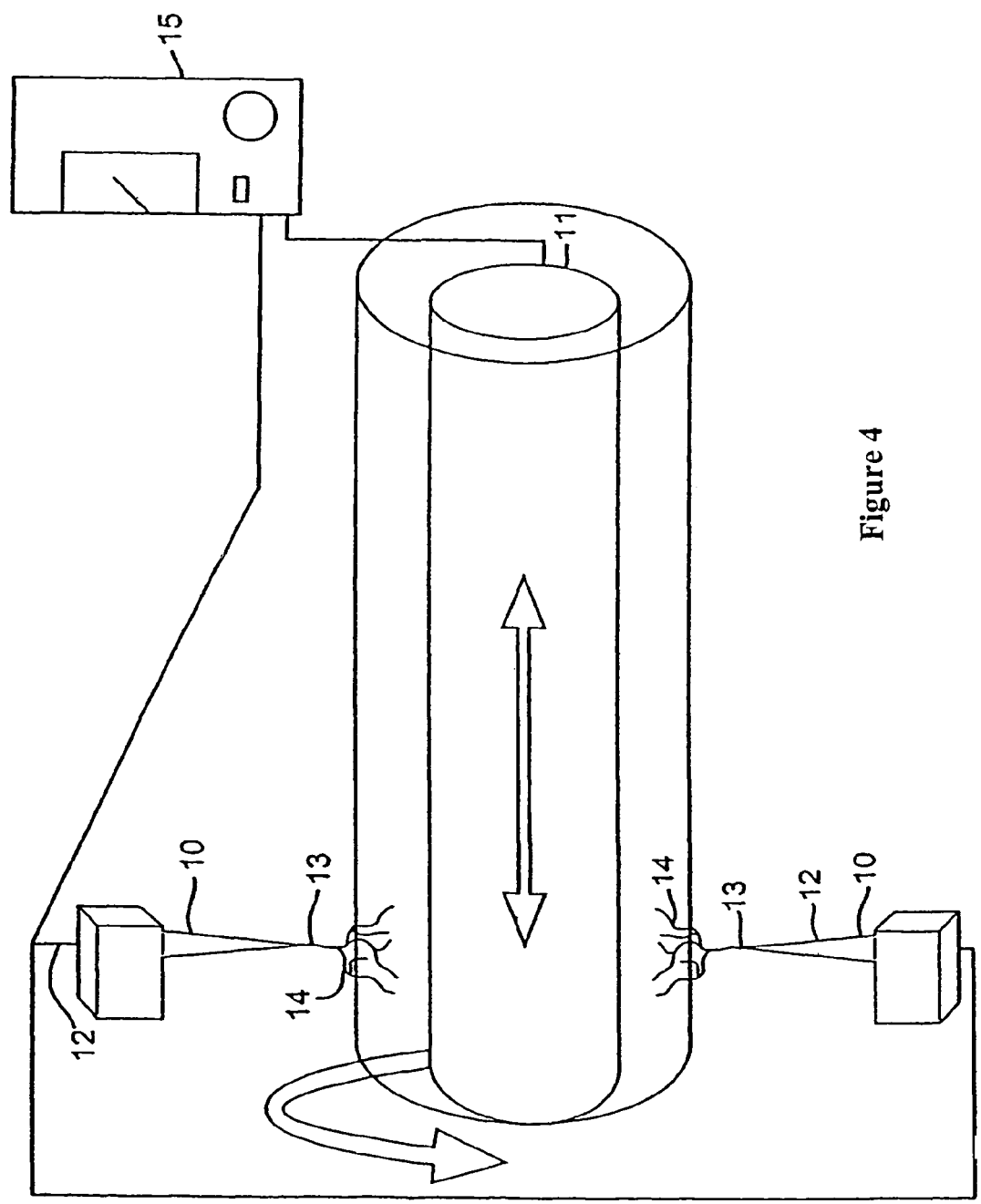
Figure 5:
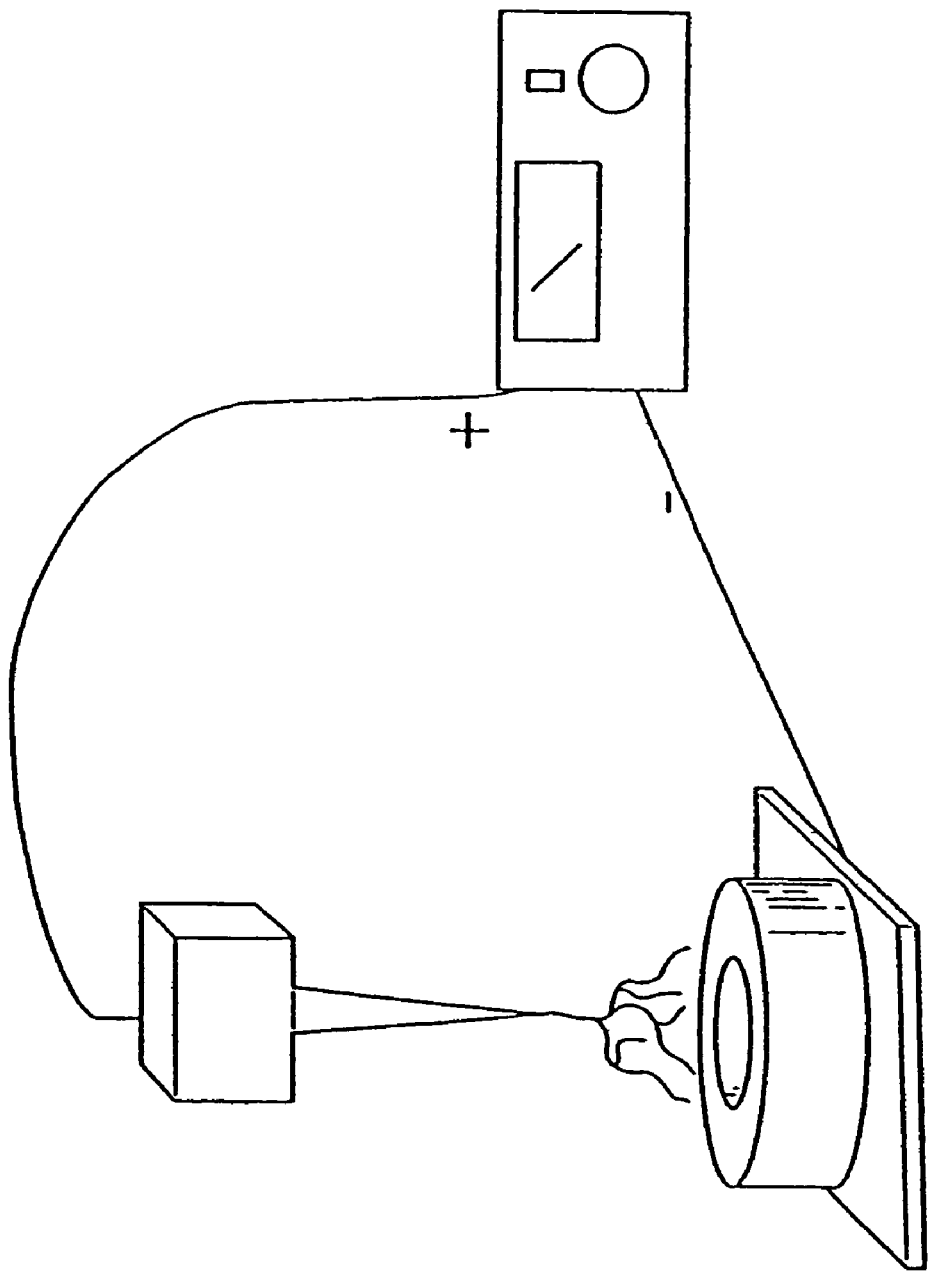
FIG. 5 is a schematic drawing of an electroprocessing devise and electroprocessed material directed to a shaped target.

An extracellular matrix of electrospun fibrin fibers, in accordance with the present invention, can be produced as described below. While any molecules capable of forming fibrin may be used, it is preferable to electrospin fibrinogen or thrombin to make fibrin fibers. Various effective conditions can be used to electrospin a fibrin fiber matrix. While the following is a description of a preferred method, other protocols can be followed to achieve the same result. Referring to FIGS. 3 and 4, in electrospinning fibrin fibers, micropipettes 10 are filled with a solution of fibrinogen or thrombin and suspended above a grounded target 11, for instance, a metal ground screen placed inside the central cylinder of the RCCS bioreactor. A fine wire 12 is placed in the solution to charge the solution in each pipette tip 13 to a high voltage. At a specific voltage determined for each solution and apparatus arrangement, the solution suspended in each pipette tip is directed towards the grounded target. This stream 14 of fibrinogen and thrombin forms a continuous filament that, upon reaching the grounded target, collects and dries to form a three-dimensional, ultra thin, interconnected matrix of fibrin fibers.

Minimal electrical current is involved in this process, and, therefore, the streaming process does not denature the fibrinogen and thrombin, because there is no expected temperature increase in the fibrinogen and thrombin solutions during the procedure.

Like the electrospinning process, an electroaerosoling process can be used to produce a dense, matte-like matrix of fibrin droplets. The electroaerosoling process is a modification of the electrospinning process in that the electroaerosol process utilizes a lower concentration of the fibrinogen and thrombin during the procedure. Instead of producing a polymeric splay (fibers) at the charge tip of the splay nozzle, small droplets of fibrinogen and/or thrombin are formed. These droplets then travel from the charged tip to the grounded substrate to form a sponge like matrix composed of fused polymeric droplets, generally in the order of less than 10 microns in diameter.

As with the electrospinning process described earlier, the electroaerosol process can be carried out using various effective conditions. The same apparatus that is used in the electrospinning process, for instance as shown in FIGS. 3 and 4, is utilized in the electroaerosol process. The differences from electrospinning include the concentration of the fibrinogen or thrombin placed in solution in the micropipette reservoir and/or the voltage used to create the stream of droplets.

One of ordinary skill in the art recognizes that changes in the concentration of fibrinogen or thrombin solutions requires modification of the specific voltages to obtain the formation and streaming of droplets from the tip of a pipette.

Various molecules can be used alone, or in combination, to produce the electrospun and/or electroaerosol fibrin matrices. Any suitable molecules that will form fibrin may be used. In preferred embodiments, fibrinogen and thrombin are employed to form the extracellular fibrin matrix. Fibrin, fibrinogen and thrombin are available from commercial sources, or they can be prepared according to methods known in the art.

Numerous molecules, cells or other materials, such as polymers, can be supplemented into the electrospinning or electroaerosoling solution. In one embodiment, naked DNA or vectors containing desired coding information for a specific product(s) can be mixed into the fibrinogen or thrombin solutions for incorporation into the tissue-engineered scaffold. Upon consumption/reorganization of the scaffolding by the seeded cells, they may incorporate the vector into their DNA and produce a desired effect. The DNA can be in any form which is effective to enhance its uptake into cells. For example, it can be naked (e.g., U.S. Pat. Nos. 5,580,859; 5,910,488) or complexed or encapsulated (e.g., U.S. Pat. Nos. 5,908,777; 5,787,567). Similar to adding DNA, antibiotics, chemotherapy agents, antifungals, analgesics, hormones, emollients, humectants, antimycotics, anti-oxidants, vitamins, conditioners, rejection drugs, other drugs, peptide growth factors including VEGF (vascular endothial growth factor), NGFs (nerve growth factors), PDGF-AA, PDGF-BB, PDGF-AB, FGFb, FGFa, and BGF (bone growth factors), monokines, immunosuppressants, angiogenic factors or other factors as discussed elsewhere herein, may be added into the electrospun or electroaerosol matrix to aid in tissue regeneration or to achieve other desired biological results.

The electrospinning or electroaerosoling process can be manipulated to meet the specific requirements for any given application of the electroprocessed fibrin made with these methods. In one embodiment, the micropipettes can be mounted on a frame that moves in the x, y and z planes with respect to the grounded substrate. The micropipettes may be mounted around a grounded substrate, for instance a tubular mandrel. In this way, the fibrinogen or thrombin streamed from the micropipette can be specifically aimed or patterned. Although the micropipettes can be moved manually, preferably, the frame onto which the micropipettes are mounted is controlled by a microprocessor and a motor that allows the pattern of streaming collagen to be predetermined by a person making a specific matrix. Such microprocessors and motors are known to one of ordinary skill in the art. For instance, fibrins fibers or droplets can be oriented in a specific direction, they can be layered, or they can be programmed to be completely random and not oriented.

In the electrospinning process, the fibrinogen and thrombin stream or streams can branch out to form fibrin fibers. The degree of branching can be varied by many factors including, but not limited to, voltage, ground geometry, distance from micropipette tip to the substrate, diameter of micropipette tip, fibrinogen concentration, and thrombin concentration. Fibrinogen, thrombin, fibrin and various combinations can also be delivered to the electric field of the system by injecting the materials into the field from a device that will cause them to aerosol. This process may be varied by many factors including, but not limited to, voltage (for example ranging from about 0 to 30,000 volts), distance from micropipette tip to the substrate (for example from 0-40 cm), and the diameter of micropipette tip (approximately 0-2 mm). Several of these variables are well-known to those of skill in the art of electrospinning microfiber textile fabrics.

The geometry of the grounded target can be modified to produce a desired matrix. In a preferred embodiment, a rotating wall bioreactor is used. The grounded target is a cylinder that fits inside the inner cylinder in the electrospinning or electroaerosoling process. By varying the ground geometry, for instance having a planar or linear or multiple points ground, the direction of the streaming fibrin can be varied and customized to a particular application. For instance, a grounded target comprising a series of parallel lines can be used to orient electrospun fibrin in a specific direction. The grounded target may be a cylindrical mandrel whereby a tubular matrix is formed. Most preferably, the ground is a variable surface that can be controlled by a microprocessor that dictates a specific ground geometry that is programmed into it. Alternatively, for instance, the ground may be mounted on a frame that moves in the x, y, and z planes with respect to a stationary micropipette tip streaming collagen. The grounded target 11 in FIG. 4 is shown as being able to oscillate along its longitudinal axis.

The substrate onto which the fibrin is streamed, sprayed or sputtered can be the grounded target itself or it can be placed between the micropipette tip and the grounded target. The substrate can be specifically shaped, for instance in the shape of a nerve guide, skin patch, fascial sheath, or a vascular graft for subsequent use in vivo. The fibrin matrix can be shaped to fit a defect or site to be filled. For example a site where a tumor has been removed, or an injury site in the skin (a cut, a biopsy site, a hole or other defect) or to reconstruct or replace a missing or shattered piece of bone. Electroprocessing allows great flexibility and makes it possible to customize the construct to virtually any shape needed. Fibrin is so flexible that it can be formed to virtually any shape.

Other variations of electroprocessing, particularly electrospinning and electroaerosoling include, but are not limited to the following:

1. Using different solutions (e.g., fibrinogen and thrombin) to produce two or more different fibers or droplets simultaneously (matrix fiber or droplet array). In this case, the single component solutions can be maintained in separate reservoirs.

2. Using mixed solutions (for example, fibrin, fibrin and cells, fibrinogen and cells, thrombin and cells, fibrinogen and growth factors, fibrinogen or thrombin and drugs) in the same reservoir(s) to produce fibers or droplets composed of multiple substances (fiber composition "blends"). Nonbiological but biologically compatible material can be mixed with a biological molecule such as fibrin, fibrinogen or thrombin, for example PVA, poly(lactic acid) (PLA), poly(glycolic acid) (PGA), PEO, etc. Other biological materials can be added, for example collagen or blends of collagen.

3. Utilizing multiple potentials applied for the different solutions or even the same solutions.

4. Providing two or more different geometric grounded targets (i.e. small and large mesh screens).

5. Placing the mold or mandrel or other ungrounded target in front of the grounded target.

6. Applying agents such as Teflon onto the target to facilitate the removal of electroprocessed materials from the target (i.e. make the material more slippery so that the electroprocessed materials do not stick to the target).

All these variations can be done separately or in combination to produce a wide variety of electrospun and electroaerosol electroprocessed fibrin extracellular matrices.

Additionally, a matrix can be formed that includes both electrospun fibrin and electroaerosol fibrin. In other words, a combination of fibers and droplets may be beneficial for some applications depending on the particular structure to be mimicked. This combination of fibers and droplets can be obtained by using the same micropipette and solution in varying the electrical charge; varying the distance from the grounded substrate; varying the polymer concentration in the reservoir; using multiple micropipettes, some from streaming fibers and others for streaming droplets; or any other variations to the method that could be envisioned by those of skill in this art. The fibers and droplets could be layered or mixed together in same layers. The construct can be fabricated in laminate layers so that each alternate layer is designed to undergo degradation, breakdown, hydrolysis after different rates. For example, the inner layer of a construct might be fabricated from electrospun fibrinogen/fibrin. This layer is then coated with collagen, then a layer of PLA, a layer of PGA or any other desired layer.

The stability, rigidity, and other attributes of the electrospun or electroaerosol matrix can be regulated by the degree to which it is chemically modified. The electrospun or electroaerosol matrix may be used in its unmodified state, or it may be modified in accordance with the requirements of a specific application. Modifications to the matrix can be made during the electrospinning or electroaerosoling process or after it is deposited. Cross-linking agents such as carbodiimide EDC (1-ethyl-3(3 dimethyl aminopropyl)), carbodiimide hydrochloride, NHS (n-hydroxysuccinimide), or UV light can be used, e.g., aldehydes (e.g. glutaraldehyde) photosensitive materials that cross link upon exposure to specific wavelengths of light, osmium tetroxide and other cross-linking fixatives.

One embodiment for appropriate conditions for electrospinning fibrin is presented below. For electrospinning fibrin by combining fibrinogen and thrombin, the appropriate approximate ranges are: voltage 0-30,000 volts; pH 7.0 to 7.4; calcium 3 to 10 mM; temperature 20 to 40° C.; ionic strength 0.12 to 0.20 M; thrombin 0.1 to 1.0 units per ml; and fibrinogen 5 to 25 mg/ml. For electrospinning fibrin monomer, the pH would start at 5 and increase to 7.4 while the ionic strength would start above 0.3 M and decrease to 0.1 M. The other conditions are similar as stated within this paragraph. Fibrin matrices of varying properties can be engineered by shifting the pH, changing the ionic strength, altering the calcium concentration or adding additional polymeric substrates or cationic materials.

Forming an Electroprocessed Fibrin Matrix

Electroprocessed fibrin can be electrodeposited inside a specifically shaped mold (FIG. 5). For instance, a particular type of organ or tissue that is desired to be replaced has a specific shape, such as a skin patch to fit a biopsy site or a large scalp area following a wide area removed after discovering a malignant melanoma That shape is then reproduced and created inside a mold designed to mimic that shape. This mold could be filled by electrodepositing the fibrin into the mold. In this way, the fibrin matrix exactly mimics the mold shape. Creating an extracellular fibrin matrix that has a specific shape can be very important in creating a new organ. The shape of the matrix can induce cells seeded into the fibrin matrix to differentiate in a specific manner. Growth factors or other substances may be incorporated as discussed elsewhere herein. This can result in a more effective, more natural-like organ or tissue being created. Hollow and solid organs can be made. Mixing cells with the material during electrospraying forms cells within the matrix so that they do not have to migrate into the gel.

An extracellular matrix of fibrin may also be created through electroprocessing techniques such as electrospinning and electroaerosoling. For this purposes of this discussion, electrospinning and electroaerosoling are terms that are used interchangeably. In order to electrospin fibrin, at least two different reservoirs are connected together at an orifice. One of the reservoirs contains fibrinogen, another contains thrombin. The solutions containing these components are mixed together immediately before they are streamed from an orifice in the electrospinning process. In this way, fibrin forms literally as the microfibers or microdroplets are formed in the electrospinning process.

Fibrinogen may also be electrosprayed into a moist atmosphere of thrombin to form filaments within the electric field. Fibrinogen may also be electrosprayed onto a target that has thrombin. Alternatively thrombin may also be electrosprayed onto a target that has fibrinogen.

An extracellular matrix incorporating fibrin can made by combining fibrin with one or more other materials and components to create a matrix. For instance, an extracellular matrix that has both collagen and or fibronectin and or other matrix materials and fibrin incorporated into it could be created. This could be useful depending on the specific type of tissue or organ being synthesized. In additional to mixing fibrin with other matrix ingredients, fibrin can be used in connection with other matrix building processes. In other words, an extruded tube could have an outside layer electrospun onto it wherein the different layers complement each other and provide an appropriate matrix to promote a specific type of cell growth. An example includes a vascular graft comprised primarily of a collagen tube. Outside the tube, an electrospun layer of both fibrin and cells could be added to promote the acceptability of the graft in a particular recipient. A second example is an in vitro skin preparation formed by growing fibroblasts in one layer, covering the first layer with electroprocessed collagen, and then growing a second layer composed of epidermal cells in the fibrin matrix. This "sandwiching" technique could be used to make a variety of tissues.

The various properties of the extracellular matrix can be adjusted in accordance with the needs and specifications of the cells to be suspended and grown within it. The porosity, for instance, can be varied in accordance with the method of making the extracellular matrix. Electrospinning a particular matrix, for instance, can be varied by fiber (droplet) size and density. If the cells to be grown in the matrix require a great deal of nutrient flow and waste expulsion, then a loose matrix could be created. On the other hand, if the tissue to be made requires a very dense environment, then a dense matrix could be designed. Porosity may be manipulated by mixing salts or other extractable agents. Removing the salt will leave holes of defined sizes in the matrix.

Uses for Electroprocessed Fibrin

There are many different applications for fibrin produced through electroprocessing methods. This versatility is enabled by the variability of the process itself. Generally speaking, there is variability with the equipment and solutions used, and various post-process treatments. One post treatment is the addition of antifibrinolytic agents to delay network dissolution and provide a more durable material. Another post-process treatment is traction alignment to apply force to the electroprocessed fibrin in order to shape or align it. This could be useful for the production of nerve guides and other objects. Fibrin or fibrinogen may be cross-linked with cross-linking agents known to one or ordinary skill in the art of cross-linking proteins, for example, with carbodiimides, aldehydes, or ultraviolet energy (if photo-sensitive agents are employed).

The use of electroprocessed fibrin as an extracellular matrix has many advantages. As a clotting agent, fibrin is associated with healing in the body. It is a porous medium that allows nutrients and waste to flow to and from cells suspended within a fibrin structure. The presence of fibrin also promotes the growth of vasculature in adjacent regions, and in many other ways is a natural healing promoter.

Fibrin is a readily available material. It is present in plasma To the extent that the extracellular matrix is being used to fabricate a tissue or organ to be transplanted into a recipient, the recipient's own plasma can be used as a source of fibrin (fibrinogen) to create the matrix. In this way, the matrix is made from a recipient's own fibrin, thereby overcoming potential complications with respect to viral exposure from materials obtained from other human donors. Use of fibrin collected from other sources can be made significantly safer by multiple purification steps, and by processes such as pasteurization or other processes to remove viral particles and other infectious agents.

Fibrin is an excellent extracellular matrix because it is eventually absorbed by the body of the recipient. In other words, during and after fibrin serves its healing/rebuilding purpose, the body will naturally degrade it. This is part of the natural healing mechanism. There would be no lingering foreign matter, only the cells constituting the replacement cells, tissues or organs. Electroprocessed fibrin may be mixed with other fibrillar materials to obtain different rates of degradation. Native fibrin degrades rapidly, collagen more slowly, PGA and PLA more slowly yet. Cross-linking the fibrin and other materials to various degrees will stabilize the materials to different extents. Electroprocessed fibrin may be slightly cross-linked for small increase in half life, or highly cross-linked to provide extended duration of use.

There are numerous applications for fibrin produced through electroprocessing methods. The different fields of use of this process and the product thereof include biomedical applications. Non-limiting examples of potential applications in these fields of use will be discussed herein.

Biomedical Applications

There are at least two major biomedical applications for fibrin produced through electroprocessing techniques. In general terms, electroprocessed fibrin matrix may be used in the formation of an extracellular matrix and in delivery of substances, including drugs.

Electroprocessed fibrin may be used in several biomedical areas, including but not limited to the following: topical wound care; temporary skin patch; skin grafts; dural patches; bed sores; ulcers, including diabetic ulcers; cuts; abrasions; fascial replacements; surgical applications for example, application such as electrospray onto a open site or surgical field; hemostatic agent to stop bleeding (sheets, paste, powders, films, and other forms); biological suture material; matrix for micro-organ production; nerve guide for nerve repair as a nerve replacement when combined with neurogenic stem cells; as a scaffold for introducing or reintroducing cells into the body. Electroprocessed fibrin may be made in a dry form ready to react upon contact with water, or timed to react after contact with water after some interval (determined by the carrier molecules used to process the fibrinogen). Hemophiliacs would especially benefit from the hemostatic properties of the electroprocessed fibrin of the present invention.

Biomedical applications of cross-linked electroprocessed fibrin include the following: vascular valves; vascular grafts; tendon/muscle repair; tendon or ligament; vascular scaffold or support; wound care; cartilage; hernia patch; nerve repair, bone; suture material; and as a bioengineering platform.

Bioengineering Using Electroprocessed Fibrin Matrix

An additional application of the invention is as a platform for the fabrication of tissue using an electroprocessed fibrin matrix as a solid support. The fabrication platform is composed of an electroprocessed matrix of fibrin, or fibrin combined with other molecules, microfibers or blends of materials. The overall three-dimensional geometric shape of the platform is determined by the ultimate design and type of tissue to be bioengineered.

Several permutations of the design are possible. For example, to fabricate a solid three-dimensional "plug" of fibrin-containing tissue, a fabrication platform is electrodeposited on a mandrel or into a mold, perhaps through electrospraying. The mandrel may be cylindrical in shape, a flattened oval shape, a rectangular envelope shape (like a mailing envelope), or any other desired shape. The fibrin-containing bioengineering platform is electrodeposited on a mandrel with the desired shape and allowed to cure. The electrodeposited matrix is removed from the mandrel. For a cylindrical-shaped bioengineering platform or any other shape of construct in which an enclosed area is desired, a suture, glue, staple or heat seal or some other method may be used to seal one end of the bioengineering platform. This results in a hollow platform that is closed on one end and open on the other. The electrodeposited fibrin-containing platform can now be filled with cells or other materials, or cells or other materials may be placed on the outer surface of the construct. For example, a mixture of fibrin from the electroprocessing procedure, or other materials such as cells, or molecules such as drugs or growth factors may be placed within the platform. The free and open end of the envelope that was used to fill the construct with material can be sutured, glued or heat sealed shut to produce an enclosed bioengineering platform. The entire construct is then placed into a bioreactor for cell culture or directly placed in situ for further development. With modifications, a bioengineering fibrin-containing platform composed of a solid, rather than a hollow, format can be electroprocessed.

Endothelial cells may be added to the core or outside surface of the fibrin-containing bioengineering platform during seeding to pre-form a capillary network.

Cells may be added during the electroprocessing process to trap or surround cells within the fibrin matrix as it forms. This may be accomplished by adding cells from a separate nozzle(s) or other sources if the materials to be electroprocessed, for example fibrinogen and thrombin, must be placed in an organic solvent or solvents (for example a solvent with high or low pH or a solvent with high or low salt content). Cells may also be added by other means, for example cells may be dribbled into an electrospinning stream and trapped by the forming fibers.

Cell polarity can be regulated by controlling the orientation of the fibrin fibers on the mandrel during or after electroprocessing. For aligned fibers, this can be accomplished by electrodepositing, perhaps using electrospinning, onto a target mandrel that is spinning. The fibrin fibers will be wrapped around the mandrel in the direction of rotation. Electrospinning onto a static, non-spinning mandrel will produce a more random fibrillar matrix. Fibrin can be mechanically aligned after spinning by stretching or some other form of mechanical distension. Orientation of the electroprocessed fibrin matrix may be beneficial in facilitating cell proliferation.

Polarity may also be controlled by first electroprocessing an aligned matrix onto a spinning mandrel. The matrix is then cut from the mandrel, rotated 90 degrees (or any other degree of rotation) and placed back onto a mandrel. A second layer of material is then electrospun onto the first layer. This method will produce an inner layer of fibrin fibers that are aligned along the long axis of rotation. Alternatively, fibrin layers created with this method may be surrounded by layers of other materials. These materials may include biocompatible materials such as PGA, PLA, PGA:PLA co-polymers.

Cell polarity can be regulated by placing the bioengineering platform within a stretching device installed in the bioreactor. By gradually applying strain across the construct over time the cells within the platform will spread in parallel with the applied force.

Cells may also be electrodeposited with the electroprocessed fibrin, either from the same reservoir or from different reservoirs. The electroprocessed fibrin bioengineering platform may be used as a differentiation platform for the manipulation of cells such as stem cells. The porosity and chemical composition of the electroprocessed fibrin matrix can be controlled prior, during, and after fabrication. This permits creation of a desired microenvironment that is believed to be critical for controlling the differentiation process in stem cells.

Conductive materials may be electrodeposited into or onto the electroprocessed fibrin matrix. In this way the fibrin-containing construct can be electrically stimulated to promote neural ingrowth, stem cell differentiation, or contraction of engineered muscle, or to promote the formation of bone in orthopedic applications where fibrin is used as a carrier to reconstruct bone. Incorporating conductive materials into an fibrin matrix produced through electroprocessing also could be used as means to further alter the properties of a fibrin matrix following fabrication. For example, applying an electrical field across an existing fibrin matrix might be used to alter the shape, porosity or density of the matrix. The stability of the fibrin matrix (resistance to breakdown) might be altered by applying an electric field across the fibrin. Magnetic materials can be placed in the matrix to allow the matrix to be moved. For example, a magnetic field can be used to position a matrix by relatively non-invasive means, to direct the movement of the matrix within the peritoneum. Such materials include but are not limited to carbon black or graphite, carbon nanotubes, ferrofluids, and various dispersions of electrically conducting polymers. Also, conducting polymer fibers can be produced by electrospinning during fibrin electroprocessing. In addition, conducting polymers can be prepared in-situ in the fibrin by, for example, incorporation of a monomer (e.g., pyrrole) followed treatment with polymerization initiator and oxidant (e.g., $FeCl_3$). Finally, conducting polymers can be grown in fibrin after electroprocessing by using a fibrin-coated conductor as the anode for electrochemical synthesis of, for example, polypyrrole or polyaniline. Fibrinogen can be added to an aqueous solution of pyrrole or aniline to create a conducting polymer at the anode with entrapped fibrinogen which can then be treated with thrombin.

The fibrin-containing engineered tissue can be vascularized through different means. Angiogenic factors mat be seeded into the electroprocessed fibrin. Electroprocessed fibrin-containing engineered tissue may be vascularized by placing it within the omentum.

The fibrin-containing engineered tissue can be placed in a bioreactor to engineer an organ or alter the gene profile of cells. For example, cells may be obtained from a patient, the patient's fibrin could be electroprocessed from the patient's plasma, and this electroprocessed fibrin matrix can be used to support cells isolated from the patient. These cells could be transfected, cultured, characterized and implanted into the patient. Using this approach, only the patient's own materials are used, thereby minimizing chances of rejection. Transfections may be expressed in a temporary or permanent manner depending on the desired application.

In the present invention, cells are initially cultured by routine techniques. Once an appropriate cell density has been achieved, the cells are suspended in a solution of fibrin prior to electroprocessing. Alternatively, cells are suspended in fibrinogen or thrombin solutions prior to electroprocessing the suspension. If cells are suspended in fibrinogen, this suspension may be electroprocessed, for example sprayed or spun, and a thrombin solution may separately be sprayed into the fibrinogen spray or sprayed on the target covered by the cells suspended in fibrinogen. Fibrin, therefore, is formed in the mixed sprays or on the target. This three-dimensional fibrin structure with the cells implanted in it is then returned to a cell culture apparatus for continued growth. As is demonstrated in the following examples, the cells attach to the fibrin network and rapidly concentrate themselves. Depending on the type of cells suspended in the matrix, the cells can be promoted to grow in the same biological appearance as the normal tissue or organ corresponding to the cell type.

This electroprocessed fibrin-containing tissue provides several advantages. It provides a solid support that can be used to grow tissue at very high density. This can be achieved by simply collapsing a fibrin matrix either mechanically or chemically. This has advantages if the "growth" phase and "use/service" phase of the cells in question require different cell densities. For instance, growing cells can be made more efficient when more dilute, in term of nutrient and gas transport. When the growth phase is done, the cells can be concentrated by collapsing the matrix thus providing with a concentrated cell "plug" ready for implant or other testing. This electroprocessed fibrin-containing matrix controls and establishes a local microenvironment with the construct. By controlling material properties of the matrix, one can control the buoyant nature of the construct, the porosity and the stability of the matrix (i.e. it can be designed to be very stable or to degrade over a relatively short period of time). It provides a platform for cell culture or tissue bioengineering that is unique and amenable for use in a bioreactor environment. It also provides a platform for cell culture and bioengineering of many different types of tissues that are large and can be manipulated manually. Also, the electroprocessed fibrin-containing matrix provides a solid phase delivery device for peptide growth factors, drugs and gene sequences, partial gene sequences in the sense and anti-sense directions.

The present invention describes a technique that allows three-dimensional cell growth and tissue/organ synthesis. By mimicking the pathologic process of metastasis, cells are placed in an electroprocessed three-dimensional fibrin matrix to support growth and normal cell to cell interactions. Cells may grow at a rapid rate in these fibrin structures, and may assume the shapes seen in normal tissue and organs.

Cell Encapsulation in the Electroprocessed Fibrin Matrix

In many of the electroprocessing applications used in testing, organic solvents must be used to carry molecules capable of forming fibrin for the fabrication of an electroprocessed fibrin matrix for bioengineering. However, there are many applications in which it would be desirable to incorporate cells within the fibrin matrix during the fibrin electroprocessing process. For example, during the fabrication of bioengineered cartilage or bone, it would be desirable to entrap the resident cells of these tissues within the electroprocessed fibrin matrix as it is fabricated. This is not possible with many of the solvents that are most effective for producing the matrix for bioengineering. By suspending cells in a fibrinogen solution or within a fibrin matrix (for example a partially or fully polymerized matrix of fibrin) they may be delivered to an electroprocessed fibrin matrix during the fabrication of the fibrin.

The matrix can also be treated or seeded with various factors and proteins to control the degradation/absorption of the matrix into a recipient environment. For instance, if the cells seeded within the matrix are slow-growing, then it is beneficial to maintain the matrix integrity for enough time to allow the cells to regenerate and grow. On the other hand, if the cells are able to quickly reproduce and grow, then a short lived matrix could be desirable. Varying the concentration of aprotinin additives, aminocaproic acid, or similar fibrinolytic inhibitors or varying the degree of chemical or ultraviolet cross-linking in the matrix could be used to precisely control this variable. The matrix could also be seeded with varying growth factors, including but not limited to, angiogenesis factors, to promote a growth of blood vessels upon implantation, nerve growth factors to promote nerve growth, bone growth factors to promote bone formation, and PDGF isomers to promote cell division. The fibrin-containing matrix may be seeded with factors to promote healing, to minimize immunorejection. The fibrin-containing matrix may be seeded with agents that can induce inflammation and subsequent healing or promote the formation of a fibrotic capsule (PGA). Other agents that may be added include but are not limited to the following: suppressors of inflammation like cortisone; other anti-inflammatory drugs; hormones; cyclosporin and other anti-rejection agents; and full and partial length gene sequences both in the sense and anti-sense directions. For example, VEGF in the sense direction in a matrix that is used as a topical application to a wound. The gene sequence is delivered to cells in the immediate vicinity of the injury, transfects those cells transiently or permanently. Antisense sequences directed against proteases may be employed. In this application the antisense sequences may be full length or partial length, or mixtures of several. When delivered, these antisense sequences suppress the expression of the target molecule in a transient fashion.

Cells may be placed within the electroprocessed fibrin matrix as it is undergoing fabrication. Cells may be co-deposited with electroprocessed fibrin from the same solution of fibrin or molecules capable of forming fibrin, such as fibrinogen or thrombin. In another embodiment, a secondary source of cells can be delivered to the fibrin matrix during electroprocessing. In one embodiment, cells may be dribbled onto the mandrel during electroprocessing of fibrin.

Cells may be suspended within an aerosol as a delivery system for the cells to the electroprocessed fibrin matrix. The cells may be delivered in this manner while the fibrin matrix is being formed. Cardiac fibroblasts were suspended in phosphate-buffered saline (PBS) at a concentration of approximately one million cells per milliliter. The suspension of cells was placed within a reservoir of a Paasche air brush. To test the efficacy of using this type of device to deliver cells we initially sprayed the cell suspension onto a 100 mm culture dish. Some of the cells survived, attached to the dish and spread out over the substratum.

In the second trial the culture dish was located further away from the air brush and the experiment was repeated. Cells were observed on the dish. They appeared to be flattened by the impact and were partially spread out over the surface of the substratum. Culture media was added to the dish and the cells were placed into an incubator. After one hour of culture, the cells were re-inspected and many were found to have spread out further over the substratum. These results demonstrate that a simple airbrush device can be used to place cells into an aerosol droplet and deliver them on demand to a surface or site of interest. Cell viability may be improved by restricting this technique to cells that are resistant to the shear forces produced in the technique, developing a cell suspension with additives that cushions the cells or refining the aerosolizing device to produce a more laminar flow. In addition directing the cell aerosol into fibrin filaments as they are undergoing polymerization in the air gap between the mandrel and source(s) of molecules capable of forming electroprocessed fibrin would cushion the cells. While not wanting to be bound by the following statement, it is believed that the cells will be trapped in the filament storm produced by electrospinning or electroprocessing and pulled onto the mandrel. This should be less traumatic to the cells than directly spraying the cells onto a solid surface.

An alternative method to deliver cells to the fibrin matrix involves electroaerosol delivery of the cells. Cells can be deposited by electrostatic spraying at 8 kV directly onto standard polystyrene culture dishes, suggesting that electrostatic cell spraying is a viable approach. We have also electroaerosoled cardiac fibroblasts in PBS up to a 20 Kv potential difference.

Schwann cells (rat) were plated on a PS petri dish by conventional methods after one day. Schwann cells were also electrosprayed onto a PS petri dish with a metal ground plate behind the dish at 10 kV after one day. Both samples grew to almost confluence after one week. This provides some distinct advantages. First, the shear forces produced during the delivery phase (i.e. the production of the aerosol) appear to be much less traumatic to the cells. Second, the direction of the aerosol can be controlled with a high degree of fidelity. In essence the cell aerosol can be "painted" onto the surface of interest. This allows the cell to be targeted to specific sites. In electroaerosol delivery, cells are suspended in an appropriate media (e.g. culture media, physiological salts etc) and charged to a voltage, and directed towards a grounded target. This process is very similar to that used in electroprocessing, particularly electrospinning. The produces a fine mist of cells trapped within the droplets as they are produced and directed at the grounded target.

Cells may be delivered using aerosol and electroaerosol techniques onto an matrix forming by electroprocessing techniques, for example a fibrin matrix that is undergoing electrodeposition, perhaps via electrospinning. The electroaerosol of cells might be delivered in parallel (i.e. along side the electrospinning fibrin) with the electrospun fibrin matrix or from a separate site. The cells may be delivered to the filament storm produced within the air gap in the fibrin electrospinning process or directed at the target. The cells and electroprocessed fibrin matrix also may be delivered in an alternative fashion to the target, i.e. electrodeposit the matrix, aerosol the cells, electrodeposit the matrix, aerosol the cells. This would allow for the discreet layering of the construct in separate layers. A vapor source could be provided that directs water onto the mandrel of target used to collect the cells. This would improve viability by keeping the cells from dehydrating during processing.

Cells might be added to the electroprocessed fibrin matrix at any time or from any orientation in any aerosol strategy. A final consideration is that an aerosol of cells or other materials, such as drugs, coagulation factors, anti-inflammatories, growth factors, antibacterials, or DNA, might be delivered directly to an in situ site. For example, an electroprocessed fibrin matrix, perhaps an electrospun fibrin matrix might be produced directly onto a skin wound, with or without cells. Then additional cells or materials might be aerosolized onto or into the wound site. Other surgical sites may also be amenable the delivery of materials using various electrodeposition techniques such as electroaerosol, electrospinning, electrosputtering, electrospraying or a combination of these methods.

Yet another embodiment for cell delivery that has many potential applications is to trap cells or drugs within a carrier prior to producing an aerosol. For example, cells or drugs or other materials might be encapsulated within a material like alginate. The encapsulated cells would be physically protected from shear and trauma during processing. Cells delivered in this form to the electroprocessed fibrin matrix would be expected to have higher viability when sprayed or electrostatically seeded. This type of strategy can also be used to specify release profiles of entrapped materials, like drugs or peptides that may not interact with the fibrin fibers used in electroprocessing. For example, a drug like penicillin might not bind or interact with an electrospun matrix of fibrin. However, the drug could be entrapped in PGA pellets, PLA pellets or even electroaerosoled to produce pellets into the electrospun matrix of fibrin. The pellets or electroaerosoled droplets containing the penicillin would begin to dissolve to deliver the entrapped material. The release profile can be tailored by the composition of the material used in the process. In addition to delivery of cells, fragmented cell debris or cell fragments may alternatively be delivered to the electroprocessed fibrin matrix, in the presence or absence of intact cells. Cell fragments are known to promote healing in some tissues. Thus, in some applications it may be desirable to incorporate cellular debris into the electroprocessed fibrin matrix, either directly within the fibrin forming solutions during electroprocessing, or indirectly from a separate source.

The foregoing discussion has been limited to specifics with respect to building an electroprocessed extracellular fibrin matrix. In order to build tissue or organs (or organ-like tissue), it is necessary to add cells to the matrix. Preferably, the cells are added either before or at the same time as the fibrinogen and thrombin mixtures are brought together. In this way, the cells are suspended throughout the three-dimensional matrix. Typically, the cells are included in the mixture that contains the fibrinogen (whether it is plasma or purified fibrinogen). When the fibrinogen and thrombin are brought together immediately prior to insertion into a mold, or immediately prior to the streaming step in the electrospinning process, the result is a good distribution of cells in suspension in the resulting extracellular matrix. Cells may also sprayed or dribbled into the forming matrix and thereby trapped as the matrix crosses the air gap between the source solutions and target.

Many types of cells can be used to create tissue or organs. Stem cells, committed stem cells, and/or differentiated cells may be used. Also, depending on the type of tissue or organ being made, specific types of committed stem cells can be used. For instance, myoblast cells can be used to build various muscle structures, neuroblasts can be employed to build nerves, osteoblasts are chosen to build bone. Other types of committed stem cells, and stem cells including uncommitted, and embryonic stem cells, bone marrow stem cells and umbilical cord stem cells can be used to make organs or organ-like tissue such as livers, kidneys, etc. Also differentiated cells, like fibroblasts can be used in fibrin matrix to make a patch, for example a hernia patch, endothelial cells for skin, osteoblasts for bone, and differentiated cells like cadaver donor pancreatic islet cells (using the fibrin as a solid phase) for a delivery device to place these cells in a specific site, for example the liver. As noted earlier, the shape of the fibrin-containing extracellular matrix may help send signals to the cells to grow and reproduce in a specific type of desired way. Other factors and differentiation inducers may be added to the matrix to promote specific types of cell growth. Further, there may be different mixtures of cell types that are incorporated into the extracellular matrix. This could be used to enhance, for instance, the vascularization of the resulting "organ" or "organ-like" tissue.

In certain disease states, organs are scarred to the point of being dysfunctional. A classic example is cirrhosis. In cirrhosis, normal hepatocytes are trapped in fibrous bands of scar tissue. With the techniques described herein, the diseased liver could be biopsied, viable liver cells obtained, grown in this new electroprocessed fibrin-containing extracellular matrix, and re-implanted in the patient as a bridge to or replacement for routine liver transplantations.

Mixing of committed cell lines in a three dimensional matrix can be used to produce structures that mimic complex organs. By growing glucagon secreting cells, insulin secreting cells, somatostatin secreting cells, and/or pancreatic polypeptide secreting cells, or combinations thereof, in separate cultures, and then mixing them together in a fibrin matrix through electroprocessing, an artificial pancreatic islet is created. These structures could then be placed under the skin, retroperitoneally, intrahepatically or in other desirable locations, as implantable, long-term treatments for diabetes.

Other non-limiting applications include hormone-producing cells. Numerous applications fall within this category; for example, replacement of anterior pituitary cells to affect synthesis and secretion of growth hormone secretion, luteinizing hormone, follicle stimulating hormone, prolactin and thyroid stimulating hormone, among others. Gonadal cells, such as Leydig cells and follicular cells may be employed to supplement testosterone or estrogen levels. Specially designed combinations may be useful in hormone replacement therapy in post and perimenopausal women, or in men following decline in endogenous testosterone secretion. Dopamine-producing neurons may be used and implanted in a fibrin matrix to supplement defective or damaged dopamine cells in the substantia nigra. A patient's own stem cells or other stem cells may be mixed with slightly damaged cells, for example pancreatic islet cells, or hepatocytes, and placed in an electroprocessed fibrin matrix and later harvested control the differentiation of the stem cells into a desired cell type. This could be done in vitro or in vivo. The newly formed differentiated cells may then be introduced into the patient.

Substance Delivery Using Electroprocessed Fibrin

In addition, depending upon the application, substances including but not limited to drugs, anti-oxidants, vitamins, cosmetics, nucleic acids, vectors, wound care products, and hormones might be delivered and confined to a relatively local environment using electroprocessed fibrin. Other substances and drugs include the following non-limiting list: antibiotics, antibacterials, anti-inflammatories or substances that promote healing, antibiotics, antimycotics, chemotherapy agents, antifungals, analgesics, hormones, emollients, humectants, anti-oxidants, vitamins, rejection drugs, and conditioners. Some preferred drugs or substances include, but are not limited to, estrogen, androgen, cortisone, cyclosporin, peptide growth factors including VEGF (vascular endothial growth factor), NGFs (nerve growth factors), PDGF-AA, PDGF-BB, PDGF-AB, FGFb, FGFa, and BGF (bone growth factors). It is to be understood that any desired substance or drug may be combined with the electroprocessed fibrin. In the following paragraphs, drug and substance may be used interchangeably.

For example, for a pressure ulcer (e.g. bedsore) a drug or drugs might be delivered to a topical site by an electroprocessed fibrin matrix. In effect, the electroprocessed fibrin matrix would function as a biologically compatible bandage that delivered drugs without need to remove it because it would breakdown and dissolve naturally. For more general drug delivery throughout a system, the electroprocessed fibrin matrix might be inserted into a body cavity or placed in a sub-dermal domain. In all cases the release of the drug could be tailored to be local or systemic, sustained or more transient.

An electroprocessed fibrin matrix may be used to deliver drugs (or again other agents that must be released in a controlled manner in other applications) in a variety of different ways. There is no limitation to the number of nozzles or solvent reservoirs that might be used in the processing of materials in this process.

Drug molecules may be mixed in the solvent carriers used to prepare fibrin for electroprocessing. In this system biologically compatible synthetic polymers (e.g. PLA or PGA, polymer blends or other polymers), naturally occurring polymers (e.g. fibrinogen, thrombin, fibrin or other molecules capable of forming fibrin, or synthetic polymers of natural materials) might be mixed with various drugs and directly electroprocessed. The resulting electroprocessed fibrin-containing matrix could be topically applied to a specific site, drugs would be released from the matrix as a function of the fibrin undergoing breakdown in the surrounding environment. The state of the electroprocessed fibrin in relation to the incorporated drugs is dictated and could be controlled by the chemistry of the system and varies by the fibrin forming solvent(s), and the drug solubility. These parameters can be manipulated to control the release of the drugs (or other elements into the surrounding environment). The electroprocessed fibrin-containing matrix can also be fabricated by electrospray or a mixture of electrospray and electrospinning, or any other permutation. This approach provides another level of control for the delivery of a drug.

In another embodiment, the drug is purposefully fabricated as a collection of aggregates in suspension with the substrates used for electroprocessing fibrin. Electroprocessing this type of solution incorporates the drug particles physically within the electroprocessed fibrin matrix. Release of the drug molecules from the electroprocessed fibrin matrix is a function of fibrin breakdown and the dissolution of the drug particles into the surrounding environment. Using the same drug in solution, rather than suspension, during the electroprocessing process can be expected to exhibit a different pattern of release and yet another level of control for the process. In other examples, particles of the drug might can be trapped within the electroprocessed fibrin matrix. Release would be dictated by a complex interplay of aggregation, dissolution and fibrin matrix breakdown.

In other examples it might be desirable to covalently or chemically bond a drug molecule to the electroprocessed fibrin or fibrinogen. In theory, such molecules might only be released as the polymer carrier underwent hydrolytic or enzymatic breakdown. This application is particularly attractive for biomedical engineering or other surgical applications. Drugs such as angiogenic peptides and neural growth factors might be coupled to the polymer backbone of a electroprocessed fibrin matrix used to support an engineered tissue. Again as the fibrin matrix underwent dissolution, the peptides would be released in a controlled manner in a localized domain in a gradient. The formation of peptide gradients is a critical regulatory component of many biological processes, for example in neovasculogenesis. In surgical applications, anti-vascular peptides or anti-sense oligonucleotides might be incorporated into an electroprocessed fibrin matrix that is then wrapped around a tumor that is inaccessible to conventional treatments. Release of the anti-vascular substances would suppress tumor growth. In another use, sense and antisense oligonucleotides (genetic material but not full length genes) are used to promote or inhibit cell function for a period of time. For example, an antisense oligonucleotide could be used in an electroprocessed fibrin matrix to suppress the expression of a deleterious enzyme in a wound. One target is the enzyme class called MMPs that are over expressed in chronic wounds.

Drugs might also be prepared as particles, an aerosol or perhaps a vapor. An electroprocessed fibrin matrix might be spun through these materials to passively trap the drugs to be delivered within the fibrin matrix. The process depends on the physical entrapment of particles or molecules within the fibrin matrix. Large objects, like cells or tablets, could be trapped in the matrix using this approach. This later conception of the idea could be accomplished simply by dropping materials onto or through a stream or fibrin forming solutions as an electroprocessed fibrin matrix is fabricated.

Control of drug release from the electroprocessed fibrin matrix may be further regulated by strain or by incorporating magnetic materials or electrically conductive materials into the fibrin matrix as it is electroprocessed. Applying mechanical forces to an electrospun matrix can hasten its breakdown by altering the crystallinity of the material. Similar changes in stability might be achieved by incorporating materials that are magnetically sensitive or electrically sensitive into a matrix as it is electroprocessed. A magnetic or electric field might then be subsequently applied across the electroprocessed fibrin matrix to stimulate movement or conformational changes in the matrix that subsequently stimulate the release of material from the electroprocessed fibrin matrix. This could be accomplished by directly altering the arrangement of the electroprocessed fibrin matrix to make it adopt a conformation more favorable for drug release.

Magnetic or electrically sensitive materials placed in a sub-dermal location or other location might be used to deliver drugs over a long interval of time. For example, an electroprocessed fibrin matrix that had magnetic or electrical properties and insulin might be fabricated and placed subdermally in an inconspicuous site. By passing a magnetic field or an electrical field across the electroprocessed fibrin matrix, drug release could be induced. This could be used to deliver drugs in a controlled fashion over a long period of time from the electroprocessed fibrin matrix.

Another variation of this theme is to fabricate an electroprocessed fibrin matrix with electromagnetic properties that could be implanted and stimulated to exert force on the encapsulated material. For example, such a device could be used as a temporary left ventricular assist device that could be made to be permanent, or one that could be designed to dissolve over time, eliminating the need for surgery to recover the device once the heart had recovered sufficiently.

Treatment of the Electroengineered Tissue Containing Electroprocessed Fibrin

Once the electroengineered tissue containing electroprocessed fibrin and cells is assembled, the tissue can be inserted into a recipient. Alternatively, the structure can be placed into a culture to enhance the cell growth. Different types of nutrients and growth factors can be added to a culture (or administered to a recipient) in order to promote a specific type of growth of the engineered tissue. In one example, specifically in connection with the preparation of an engineered muscle tissue, the electroengineered tissue containing fibrin and cells can be mechanically or passively strained or electrically preconditioned in order to stimulate the alignment of cells to form a more functional muscle implant. In a skin patch, application of stress may facilitate orientation of the skin for use in an area such as the scalp, exposed to significant stretching force. Passive strain in this context refers to a process in which strain is induced by the cells themselves as they contract and reorganized a matrix. This is typically induced by fixing the ends of the electroengineered fibrin matrix. As the cells contract and alter the matrix the fixed ends of the matrix remain in place and thereby strain the cells as they "pull" against the isometric load. The strain not only aligns the cells, it sends signals to them with respect to growth and development. The construct can also be strained externally, i.e. the construct can be prepared and then stretched to cause mechanical alignment. Stretch is typically applied in gradual fashion over time. The fibrin can also be stretched to cause alignment in the matrix before the cells are added to the construct (i.e. form the matrix, stretch the matrix and then add the cells).

The electroengineered cell-fibrin matrix is also useful for testing various gene therapies. In other words, by working with the cells/fibrin in vitro, different types of gene therapy and manipulation can be achieved by inserting preselected DNA in the suspension (either the cells, fibrin, plasma, etc.). There is a wider range of therapeutic techniques available in vitro than when techniques are attempted to be administered in vivo. Nonviral techniques such as electroporation may be used to treat the cultured cells prior to insertion into the fibrin matrix. They may also be treated within the fibrin matrix before the electroengineered tissue is inserted into a recipient. In vitro gene transfer avoids the exposure of a recipient to viral products and avoids the potential for germ cell line viral incorporation. It avoids the problem of finding or engineering viral coats large enough to accept large genes such as the one for Factor VIII (anti-hemophilic factor). However, in vivo gene therapy may be accomplished by incorporating DNA into the fibrin as it is created through the electroprocessing techniques of the present invention, whereby some DNA will be incorporated into the in vivo cells in contact with the fibrin as the fibrin slowly degrades in vivo. This is especially true of small gene sequences, such as antisense oligonucleotides. Adding additional agents to the matrix during or after processing can be used to manipulate gene transfection rates and the efficiency of transfection. For example, adding fibronectin to the matrix will increase the pinocytotic activity of the cells and increase the uptake of materials, including gene sequences, from the surrounding matrix. Alternatively, agents conventionally used in gene transfection may be added to the matrix, such as lipofection agents.

The engineered tissue/organ allows permits the in vitro culturing of a patient's tumor cells to identify in vitro susceptibility to various types of chemotherapy and radiation therapy. This application is essentially using the matrix as a diagnostic tool. In this way, alternative chemotherapy and radiation therapy treatments may be analyzed to calculate the very best treatment for a specific patient. For instance, an engineered tissue may be manufactured that includes fibrin and cancer cells, preferably a patient's own cancer cells. Multiple samples of this tissue can then be subjected to multiple different cancer therapies. The results from different treatments can then be directly compared to each another for assessment of efficacy.

Engineered Fibrin Implant and a Bioreactor

An engineered fibrin implant can comprise one or more of the following components, although this is a non-limiting list. They are skeletal muscle, cardiac muscle, nerve guides, brain constructs as a filler for damaged/removed areas of the brain that are lost during accident or disease, cartilage scaffoldings, sheets for cosmetic repairs, skin (sheets with cells added to make a skin equivalent), vascular grafts and components thereof, sheets for topical applications (skin covering but no additional cells-just a patch), drug and substance delivery.

There are several kinds of commercially available bioreactors, devices designed to provide a low-shear, high nutrient perfusion environment. Until recently, most of the available bioreactors maintained cells in suspension and delivered nutrients and oxygen by sparging, through the use of impellers, or other means of stirring. The RCCS bioreactor (Synthecon) is a rotating wall bioreactor. It consists of a small inner cylinder, the substrate for the electrospinning process, positioned inside a larger outer cylinder. Although the electrospun or electroaerosol fibrin-containing matrix can be fabricated on the inner cylinder, other locations within the bioreactor also may be used for placement of the fibrin matrix for seeding. The gap between the inner and outer cylinders serves as the culture vessel space for cells. Culture medium is oxygenated via an external hydrophobic membrane. The low shear environment of the Synthecon RCCS bioreactor promotes cell-cell and cell-extracellular matrix (ECM) interactions without the damage or "washing away" of nutrients that occurs with active stirring or sparging. Typically, the RCCS device is operated at rotation rates of 8 up to 60 RPM, as required to maintain cells in suspension, and at less than 8 RPM (preferably 2-3 RPM) for cultures immobilized along the center shaft of the vessel. The Synthecon bioreactor can be used in a standard tissue culture incubator. These values for spin rates and other parameters may be varied depending on the specific tissue created.

Electroprocessed fibrin, particularly cross-linked electroprocessed fibrin is useful in formation of prostheses. One application of the electroprocessed fibrin is in the formation of medium and small diameter vascular prostheses. Some examples include, but are not limited to coronary vessels for bypass or graft, femoral artery, popliteal artery, brachial artery, tibial artery, radial artery or corresponding veins. The electroprocessed fibrin is useful especially when combined with endothelial cells on the inside of the vascular prosthesis, for example a collagen tube, and also when combined with fibroblasts on the outside of the collagen tube. More complicated shapes including tapered and/or branched vessels may also be constructed. All that is necessary is a different-shaped mandrel to wind the large fibers around or to orient the electrospun/electroaerosol polymer.

Combination of electroprocessed fibrin and wound polymer fibers can provide optimal growth conditions for cells. The polymer forms a basic structural matrix and the electroprocessed fibrin matrix is used to deliver the cells. This facilitates cell attachment onto the structural matrix. Furthermore the stress in the polymer can also orient fibrin fibers in the matrix providing further spatial cues for the cells.

In an alternative fabrication strategy, a cylindrical construct is electrospun onto a suitable target, for example a cylindrical mandrel. Other shapes are also possible and the shape is determined by the shape of the site that the implant is designed to be placed within. This matrix may be composed of electroprocessed fibrinogen/fibrin (for example to promote neovascularization, cellular integration and infiltration from the surrounding tissue), collagen (to promote cell infiltration and lend mechanical integrity), and other components, for example PGA, PLA, and PGA-PLA blends, PEO, PVA or other blends. The relative ratio of the different components of this construct can be tailored to specific applications (e.g. more fibrin less collagen for enhanced vascularization in a skin graft). To fabricate a cylindrical muscle the construct is filled with muscle or stem cells or other cell type and the distal ends of the electrospun constructs are sutured or sealed shut prior. The cells can be mixed with various matrix materials to enhance their distribution within the construct. For example the cells may be mixed with electroprocessed fibrin or collagen prior to insertion into the construct. The objective of this strategy is to provide additional mechanical support to the construct and provide the cells with a three dimensional matrix within the construct to promote growth. This also helps to maintain the cells in an even distribution within the construct. This method can be used to enhance the alignment of the cells within the construct. This "filling" material may be extruded directly into the cylindrical construct, as the filling is extruded, alignment occurs. Mixing endothelial cells with the other cells inserted into the construct (or other cell types) can be done to accelerate neovascularization. Another method to accomplish this objective is to electrospin endothelial cells directly into the electroprocessed fibrin matrix that aids in formation of the cylindrical sheath. The alignment of the fibers within the electrospun matrix that comprises the construct can be controlled by controlling the relative movement of the target and source solution with respect to one another. Other cell types, such as tendon fibroblasts, could be electrospun into or onto the outer surface of the construct to enhance the formation of the outer connective tissue sheath that forms the construct. Other design principles described in this document can be used in conjunction, for example the addition of peptide growth factors, antibiotics, and/or anti-rejection drugs, to the electrospun matrix. The entire construct can be cultured in a bioreactor, conventional culture or placed directly in vivo. The use of other cell types can be used to fabricate other tissue types.

Vascularization of the engineered tissue containing electroprocessed fibrin will occur in situ several days after surgery. It can be stimulated further, as mentioned above, by angiogenic and growth-promoting factors, either administered as peptides, proteins or as gene therapy. Neovascularization of an engineered construct containing electroprocessed fibrin can also be enhanced by mixing endothelial cells into the construct during fabrication. Another alternative for supplying engineered tissue containing electroprocessed fibrin with a vascular supply is to temporarily transplant the tissue into the omentum. The omentum has an extensive and rich vascular supply that could be used like a living incubator for the support of engineered tissue. The engineered tissue is removed from a bioreactor, wrapped in the omentum and supported by the diffusion of nutrients and oxygen from the surrounding tissue in the omentum. Alternatively, or in addition to this approach, engineered tissue is connected directly to the endogenous vascular supply of the omentum. A blood vessel might be partially perforated or cut or left dissected free of the omentum. The engineered tissue containing electroprocessed fibrin is wrapped around the vessel. The engineered tissue is supported by nutrients leaking from the perforated vessel or by the simple diffusion of nutrients if the vessel is left intact. Regardless of strategy, the engineered tissue is surrounded by the omentum and its rich vascular supply.

Tissue containing electroprocessed fibrin may be engineered with an endogenous vascular system. This vascular system may be composed of artificial vessels or blood vessels excised from a donor site on the transplant recipient. The engineered tissue containing electroprocessed fibrin is then assembled around the vessel. By enveloping such a vessel with the tissue during or after assembly of the engineered tissue, the engineered tissue has a vessel that can be attached to the vascular system of the recipient. In this example, a vessel in the omentum is cut, and the vessel of the engineered tissue is connected to the two free ends of the omental vessel. Blood passes from the omental vessel into the vascular system of the engineered tissue, through the tissue and drains back into the omentum vessel. By wrapping the tissue in the omentum and connecting it to an omental blood vessel, the engineered tissue is supported by the diffusion of nutrients from the omentum and the vessel incorporated into the tissue during its fabrication. After a suitable period of time the tissue is removed from the omentum and placed in the correct site in the recipient. By using this strategy the engineered tissue containing electroprocessed fibrin is supported in a nutrient rich environment during the first several days following removal from the bioreactor. The environment of the omentum also promotes the formation of new blood vessels in implanted tissue. This omental incubator strategy can be combined with the other strategies such as combining angiogenic factors in the fibrin during electroprocessing. Several options are available. First, the implants can be seeded with angioblasts and/or endothelial cells to accelerate the formation of vascular elements once the engineered tissue is placed in situ. Second, angiogenic peptides can be introduced into the engineered tissue via an osmotic pump. The use of an osmotic pump permits delivery of peptides or, as noted, angiogenic peptides or growth factors directly to the site of interest in a biologically efficient and cost-effective manner. VEGF delivered to ischemic hind limbs of rabbits accelerated capillary bed growth, increased vascular branching and improved muscular performance with respect to ischemic controls. An alternative approach is to "seed" fully differentiated tissue constructs containing electroprocessed fibrin with additional endothelial cells and or angioblasts shortly before they are implanted in situ. Incorporating angiogenic agents into the electroprocessed fibrin matrix can also be used. The gradual degradation/breakdown of the matrix will release these factors and accelerate the ingrowth of blood vessels. Nerve growth factors can be electrospun into the matrix to promote growth or neurons into the matrix and tissue.

The stem cells or other cells used to construct the implant can be isolated from the subject, or other compatible donor requiring tissue reconstruction. This provides the advantage of using cells that will not induce an immune response, because they originated with the subject (autologous tissue) requiring the reconstruction. Relatively small biopsies can be used to obtain a sufficient number of cells to construct the implant. This minimizes functional deficits and damage to endogenous tissues that serve as the donor site for the cells.

The present invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

Example 1

Cell Culture

Several types of cells are used in experiments with the fibrin and plasma:

a) Schwann cells from transgenic mice with truncated SCIP transcription factor. These cells have shown premature and excessive myelination in vivo. This line of cells was selected, because they can be easily cultured in large quantities without any special factor.

b) Primary rat Schwann cells from sciatic nerve. These cells do not divide under the following experimental conditions. Those test cells were not from a cell line.

In all cases the cells were maintained in 10.5 cm$^2$ plastic culture flasks with Dulbecco's modified pyruvate-free Eagle medium augmented with 10% bovine serum and 1% streptomycin-penicillin (Gibco BRL, Grand Island, N.Y.). The cultures were placed in an incubator at 37° C., 7% $CO_2$ and 100% relative humidity (RH).

Cells type (a) were cultured to confluence then harvested. Cells type (b) were harvested as needed. Cells type (c) were grown in subconfluent cultures for several passages. In order to remove the cells for use, the growth media was drained and the culture was treated with 1 mL trypsin-EDTA (Gibco BRL) until the cells detached from the bottom of the dish. The trypsin was then neutralized with 4 mL of fresh media and the content of the flask transferred to a centrifuge tube. The cells were concentrated by centrifugation at 130 g for 5 minutes. The supernatant was removed and the cells resuspended in fresh media to densities of about 10$^6$ cells/mL for cell type (a) and (c) and 2-5×10$^5$ cells/mL for cell type (b). These cell suspensions were used in some of the following examples.

Example 2

Preparation of Thrombin, Fibrinogen and Plasma Stock Solutions

Thrombin was obtained from Baxter as a lyophilized power and dissolved in 10 mM calcium chloride in deionized water to a concentration of 50 units/mL. Alternatively, lyophilized thrombin (Sigma, American Diagnostic, etc.) can be dissolved in 0.15 M NaCl and calcium can be added at the time of clot formation. Blood was obtained by aseptic, non-traumatic venipuncture of a normal volunteer. The blood was collected into blue top vacutainer tubes containing 3.8% sodium citrate. The citrate binding of calcium prevented coagulation of the sample. Platelet poor plasma was prepared by centrifugation at 10,000 g for five minutes. Plasma was decanted from the top of the spun tube leaving the last centimeter depth of plasma on top of the cells to minimize cellular contamination. The citrated platelet poor plasma was filtered through a 0.45 micron filter under sterile conditions to remove fine particulate. Unused portions were stored up to three weeks at 4° C. Fibrinogen was obtained from Sigma as a lyophilized powder and used immediately after dissolution in sterile 10 mM Tris buffer at pH 7.4 and 0.138 M NaCl to a concentration of 3 mg/mL (roughly the concentration in plasma).

Example 3

Orientation of Electroprocessed Fibrin and Cells

Cells are known to adapt to their environment to suit their needs. Both muscle cells and Schwann cells self-reorganize fibrin strands into a highly oriented structures. Cells in an electroprocessed fibrin matrix may be oriented through application of mechanical force.

An electroprocessed tissue comprising electroprocessed fibrin matrix and cells (fibroblasts) to be used as skin is subjected to force in the following manner. A short piece of sterile Normex string 11, a stranded polyimid polymer string from Dupont, is attached to each end of the electroprocessed tissue (FIG. 1). Each end of the Normex string 11 is then attached to a set of nylon screws 12 mating with a 5 mm thick polyethylene holder 13. There is sufficient friction between the screws 12 and the holder 13 to prevent any motion once the screws are set. The Normex strings 11 are tensioned by slightly turning the nylon screws 12 until the fibrin strains in the electroprocessed tissue show alignment under the applied strain. No other adjustments are made to the apparatus for the reminder of the experiment. A control is also performed using similar electroprocessed tissue which is not subjected to externally applied strain. The tissue subjected to force demonstrate alignment of fibroblasts and greater tensile strength than the tissue not subjected to force.

Example 4

Electroaerosol Fibrin and Cells

A diluted cell suspension 20 in plain plasma and the stock thrombin solution 21 (~1 mL of each) were loaded into separate 3 mL plastic syringes 22 (FIG. 2). The syringes 22 were inserted in separate syringe pumps and connected to a mixing tee 23 via a size 13 Tygon tube 24. A 27 gauge needle 25 terminated the outlet of the mixing tee. The needle was connected to one pole of a Spellman CZE 1000R high voltage power supply 26. The other pole was connected to a stainless steel foil 27 attached to the back of a plastic culture dish. The mixing tee 23 was placed at about 10 cm from the culture dish. Each of the pumps was set to deliver 1.15 mL/min and a potential of −10 kV was applied, causing fibrin/cell drops to travel from the tip of the needle 25 to the culture dish.

Example 5

Assessment of Biological Activity of a Substance on Cells in an Electroprocessed Fibrin Matrix A 54 year old man is diagnosed with malignant melanoma Melanoma cells are removed from the biopsy and cultured. The cultured melanoma cells are loaded into a charged syringe. In a separate experiment, cultured-melanoma cells are loaded into an aerosol device. Electroprocessed fibrin matrices are formed and the melanoma cells are electrodeposited into the forming fibrin matrix or applied to the forming fibrin matrix through an aerosol method. Fifty of these samples are produced.

Different samples of the melanoma cells in the electroprocessed fibrin matrix are subjected to a dose range of one or more putative chemotherapeutic agents for melanoma A mitotic index is calculated at selected time intervals following exposure to the chemotherapeutic agents. Trypan blue exclusion is also evaluated. The results indicate which agent suppresses mitosis of melanoma cells and affects cell viability.

Example 6

Artificial Pancreatic Islet in Electroprocessed Fibrin Matrix

A mixture of cultured insulin secreting cells is seeded into an electroprocessed fibrin matrix to form an electroprocessed fibrin-containing tissue. The electroprocessed fibrin matrix containing the insulin secreting cells is implanted into a diabetic recipient in need of insulin. This electroprocessed fibrin-containing tissue optionally further contains a vessel. The matrix is implanted into the retroperitoneal space and the vessel is anastomosed into the hepatic portal circulation. Insulin is released from the insulin-containing cell and is transmitted to the circulation.

The electroprocessed fibrin matrix containing the insulin secreting cells is optionally supplemented with cells that synthesize and secrete glucagon, somatostatin, pancreatic polypeptide, or combinations thereof, in order to mimic the hormonal complement of the pancreatic islet.

Example 7

Electroprocessed Schwann cells in an Electroprocessed Fibrin Matrix

This experiment has been performed first using a peristaltic pump and later using two syringe infusion pumps. Experiments were also performed with cells suspended in either 2-3 mg/mL fibrinogen or using human plasma.

The following describes what was done with the infusion pumps which is similar to what was done with the peristaltic pump. The cells (Weinstein Schwann) were seeded at a concentration between $10^5$ to $10^7$ into 0.4 um filtered plasma (already containing fibrinogen) or standard Eagle media augmented with 2-4 mg/mL fibrinogen. 10 uL of 10,000 kIU aprotinin was added to each mL of cell suspension to retard clot degradation. This suspension was loaded into a 3 mL plastic syringe. A second 3 mL syringe was filled with a filtered solution of thrombin between 50-200 IU/mL complemented with sufficient calcium chloride so that the final mixture would gel. These mixtures were processed under the laminar flow hood to maintain aseptic conditions.

The syringes were each mounted onto separate syringe infusion pumps. Using dual pumps permitted variation of the concentration of thrombin to fibrinogen and thus affected the clotting rate. The outlet of the syringes were connected, via short lengths of size 13 Tygon tubing, to a mixing tee. The outlet consisted of a metal syringe needle (various gauges were used, 18-27) which served as one of the electrodes in the electrospinning setup. The target consisted of a standard plastic culture dish placed at about 10 cm away from the outlet of the mixing tee. Aluminum foil was affixed to the back of the dish with tape to provide a counter electrode. To perform electrodeposition, the pumps were started (using flow rates of less than 0.25 ml/min to several mL/min) and the applied voltage was slowly increased to the point where electrodeposition proceeded (4-6 kV). The experiment was completed in less than 10 min to minimize settling of the cells inside the tubing/syringe. Following the electrodeposition, the gel was allowed to cure in the 37° C. incubator for about one hour prior to topping the dish with culture media augmented with 10 uL/mL of aprotinin. The results were analyzed and demonstrated healthy appearing Schwann cells embedded in the electroprocessed fibrin matrix.

Example 8

Delivery of Drugs in an Electroprocessed Fibrin Matrix

Different concentrations of nerve growth factor are added to fibrinogen solutions and electrosprayed in parallel with an electrosprayed thrombin solution into wells of a 96 well culture dish containing about 10,000 neuroblasts per well. These wells now contain cells and also a electroprocessed fibrin matrix containing nerve growth factor. The fibrin slowly dissolves and the neuroblasts proliferate in response to the nerve growth factor in a dose dependent manner.

In another experiment, electroprocessed fibrin matrix containing nerve growth factor is prepared in a similar manner and is inserted into a traumatized segment of the lower cervical spinal cord of an animal injured in a fall. Another animal with a similar injury receives electroprocessed fibrin matrix without nerve growth factor. The recovery rates of the animals are evaluated. The animal receiving the electroprocessed fibrin matrix containing nerve growth factor exhibits a faster recovery of motor function of the forelimbs.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

We claim:

1. Electrodeposited fibrin matrix with cells, wherein the cells are delivered to the matrix during fabrication of the electrodeposited fibrin matrix, wherein the cells are suspended in a solution comprising molecules capable of forming fibrin during delivery to the matrix, and wherein the cells are oriented through application of stretching mechanical force to the electrodeposited fibrin matrix.

2. The electrodeposited fibrin matrix with cells of claim 1, further comprising one or more substances.

3. The electrodeposited fibrin matrix with cells of claim 2, wherein the one or more substances is a growth factor, differentiation inducer, anti-oxidant, vitamin, hormone, nucleic acid, drug, peptide, emollient, humectant, conditioner or cosmetic.

4. A method of evaluating a biological response of a cell to a substance, comprising:
   applying the substance to the electrodeposited fibrin matrix with cells of claim 1; and,
   evaluating the biological response of the cell.

5. The method of claim 4, wherein the cell is a cancer cell.

6. An electrodeposited fibrin matrix with cells, wherein the cells are entrapped within the matrix during fabrication of the electrodeposited fibrin matrix, wherein the cells are suspended in a fibrinogen solution during delivery to the matrix, and wherein the cells are oriented through application of stretching mechanical force to the electrodeposited fibrin matrix.

7. The electrodeposited fibrin matrix with cells of claim 1, wherein the cells are spread in parallel with the applied stretching mechanical force.

8. The electrodeposited fibrin matrix of any one of claims 1, 6 or 7, further comprising a cross-linking agent.

9. The electrodeposited fibrin matrix of any one of claims 1, 6, or 7, further comprising calcium.

* * * * *

UNITED STATES PATENT AND TRADEMARK OFFICE
CERTIFICATE OF CORRECTION

| | | |
|---|---|---|
| PATENT NO. | : 7,759,082 B2 | Page 1 of 1 |
| APPLICATION NO. | : 10/764691 | |
| DATED | : July 20, 2010 | |
| INVENTOR(S) | : Bowlin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 438 days.

Signed and Sealed this
Eighth Day of February, 2011

David J. Kappos
*Director of the United States Patent and Trademark Office*